US009743647B2

(12) United States Patent
Wang et al.

(10) Patent No.: US 9,743,647 B2
(45) Date of Patent: *Aug. 29, 2017

(54) HUMANIZED IL-4 AND IL-4RA ANIMALS

(71) Applicant: REGENERON PHARMACEUTICALS, INC., Tarrytown, NY (US)

(72) Inventors: Li-Hsien Wang, Somers, NY (US); Yingzi Xue, Ardsley, NY (US); Andrew Murphy, Croton-on-Hudson, NY (US); Sean Stevens, San Diego, CA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/791,978

(22) Filed: Jul. 6, 2015

(65) Prior Publication Data

US 2015/0320022 A1 Nov. 12, 2015

Related U.S. Application Data

(63) Continuation of application No. 14/706,319, filed on May 7, 2015, now Pat. No. 9,565,841.

(60) Provisional application No. 61/989,757, filed on May 7, 2014.

(51) Int. Cl.
*A01K 67/027* (2006.01)
*C07K 14/54* (2006.01)
*C07K 14/715* (2006.01)

(52) U.S. Cl.
CPC ...... *A01K 67/0278* (2013.01); *C07K 14/5406* (2013.01); *C07K 14/7155* (2013.01); *A01K 2207/15* (2013.01); *A01K 2217/072* (2013.01); *A01K 2217/20* (2013.01); *A01K 2227/105* (2013.01); *A01K 2267/01* (2013.01); *A01K 2267/0368* (2013.01); *A01K 2267/0393* (2013.01)

(58) Field of Classification Search
None
See application file for complete search history.

(56) References Cited

U.S. PATENT DOCUMENTS

| 7,659,442 B2* | 2/2010 | Poueymirou ...... A01K 67/0276 800/21 |
|---|---|---|
| 2011/0016543 A1 | 1/2011 | Weinstein et al. |
| 2013/0117873 A1 | 5/2013 | Wang et al. |
| 2013/0340104 A1 | 12/2013 | Murphy |
| 2014/0056920 A1 | 2/2014 | Ardeleanu et al. |
| 2014/0271658 A1 | 9/2014 | Murphy et al. |
| 2015/0106961 A1 | 4/2015 | Rojas et al. |
| 2015/0143558 A1 | 5/2015 | McWhirter et al. |
| 2015/0143559 A1 | 5/2015 | McWhirter et al. |
| 2015/0320021 A1* | 11/2015 | Wang ................. A01K 67/0278 800/3 |

FOREIGN PATENT DOCUMENTS

| WO | 2011044050 A2 | 4/2011 |
|---|---|---|
| WO | 2012112544 A2 | 8/2012 |
| WO | 2013063556 A1 | 5/2013 |
| WO | 2013192030 A1 | 12/2013 |
| WO | 2014039782 A2 | 3/2014 |
| WO | 2015042557 A1 | 3/2015 |

OTHER PUBLICATIONS

Seki et al. J Immunol 2004;172:6158-66.*
Myburgh et al. Mole Immunol 2008;45:1327-1336.*
Kruse et al. Intl Immunol 1999;11:1956-69.*
Hall et al. Curr Protoc Cell Biol 2009;Unit-19.1217, pp. 1-23.*
Mueller, T. et al., "Structure, binding, and antagonists in the IL-4/IL-13 receptor system" Biochim Biophys Acta (2002) pp. 237-250, vol. 1592.
Andrews, R. et al., "Reconstitution of a functional human type II IL-4/IL-13 receptor in mouse B cells: demonstration of species specificity" J Immunol. (2001) pp. 1716-1722, vol. 166.
Blaeser, F. et al., "Targeted inactivation of the IL-4 receptor a chain I4R motif promotes allergic airway inflammation" J Exp Med (Oct. 2003) pp. 1189-1200, vol. 198, No. 8.
Liu, F. et al., "Hydrodynamics-based transfection in animals by systemic administration of plasmid DNA" Gene Therapy (1999) pp. 1258-1266, vol. 6.
Moon, H. et al., "Regulation of IgG1 and IgE synthesis by interleukin 4 in mouse B cells" Scand J. Immunol (1989) pp. 355-361, vol. 30.

(Continued)

*Primary Examiner* — Janice Li
(74) *Attorney, Agent, or Firm* — Scully, Scott, Murphy & Presser, P.C.; Neil Miyamoto

(57) ABSTRACT

Non-human animals comprising a human or humanized IL-4 and/or IL-4Rα nucleic acid sequence are provided. Non-human animals that comprise a replacement of the endogenous IL-4 gene and/or IL-4Rα gene with a human IL-4 gene and/or IL-4Rα gene in whole or in part, and methods for making and using the non-human animals, are described. Non-human animals comprising a human or humanized IL-4 gene under control of non-human IL-4 regulatory elements is also provided, including non-human animals that have a replacement of non-human IL-4-encoding sequence with human IL-4-encoding sequence at an endogenous non-human IL-4 locus. Non-human animals comprising a human or humanized IL-4Rα gene under control of non-human IL-4Rα regulatory elements is also provided, including non-human animals that have a replacement of non-human IL-4Rα-encoding sequence with human or humanized IL-4Rα-encoding sequence at an endogenous non-human C IL-4Rα locus. Non-human animals comprising human or humanized IL-4 gene and/or IL-4Rα sequences, wherein the non-human animals are rodents, e.g., mice or rats, are provided.

8 Claims, 12 Drawing Sheets

(56) References Cited

OTHER PUBLICATIONS

Fort, M. et al., "IL-25 induces IL-4, IL-5, and IL-13 and Th2-associated pathologies in vivo" Immunity (Dec. 2001) pp. 985-995, vol. 15, No. 6.

Willinger, T. et al., "Human IL-3/GM-CSF knock-in mice support human alveolar macrophage development and human immune responses in the lung" PNAS (2011) pp. 2390-2395, vol. 108, No. 6.

Willinger, T. et al., "Improving human hemato-lymphoid-system mice by cytokine knock-in gene replacement" Trends in Immunology (2011) pp. 321-327, vol. 32, No. 7.

Rongvaux, A. et al., "Human thrombopoietin knockin mice efficiently support human hematopoiesis in vivo" PNAS (2011) pp. 2378-2383, vol. 108, No. 6.

Anderson, P., "Post-transcriptional control of cytokine production" Nature Immunology (Apr. 2008) pp. 353-359, vol. 9, No. 4.

Kruse S. et al., "Characterization of the Membrane-Bound and a Soluble Form of Human IL-4 Receptor a Produced by Alternative Splicing", International Immunology 11(12):1965-1969 (Dec. 1, 1999).

International Search Report and Written Opinion dated Sep. 11, 2015 received from Application No. PCT/US2015/029638.

European Office Action dated Jun. 20, 2016 received in European Patent Application No. 15 727 106.5.

GenBank NCBI Reference Sequence No. NM_001008700.3 (6 pages) (Feb. 15, 2015).

GenBank NCBI Reference Sequence No. NM_000418.3 (7 pages) (Apr. 23, 2016).

Chen Q. et al., "GM-CSF and IL-4 Stimulate Antibody Responses in Humanized Mice by Promoting T, B, and Dendritic Cell Maturation", The Journal of Immunology 189(11):5223-5229 (Oct. 22, 2012).

Partial International Search Report dated Aug. 4, 2015 received from Application No. PCT/US2015/029638.

\* cited by examiner

HUMANIZED IL-4 AND IL-4RA ANIMALS

CROSS REFERENCE TO RELATED APPLICATIONS

This application is a continuation of U.S. patent application Ser. No. 14/706,319, filed May 7, 2015, which claims the benefit of priority to U.S. Provisional Application No. 61/989,757 filed May 7, 2014, the entire contents of which are incorporated herein by reference.

INCORPORATION BY REFERENCE OF SEQUENCE LISTING

The Sequence Listing in an ASCII text file, named 31260_SEQ3.txt of 16 KB, created on Jul. 24, 2015, and submitted to the United States Patent and Trademark Office via EFS-Web, is incorporated herein by reference.

FIELD OF INVENTION

Non-human animals are disclosed herein which comprise nucleic acid sequences encoding an IL-4 and/or an IL-4Rα protein that comprise a human sequence. Transgenic non-human animals are also disclosed herein which comprise an IL-4 and/or an IL-4Rα gene that is human in whole or in part. Non-human animals that express human or humanized IL-4 and/or IL-4Rα proteins are also disclosed. In addition, methods are disclosed for making and using non-human animals comprising human or humanized IL-4 and/or IL-4Rα nucleic acid sequences.

BACKGROUND

IL-4 and IL-4Rα are therapeutic targets for treatment of a variety of human diseases, disorders and conditions that are associated with abnormal type-2 T helper (Th2) cells. The evaluation of pharmacokinetics (PK) and pharmacodynamics (PD) of therapeutic molecules that specifically target human IL-4 or human IL-4Rα proteins are routinely performed in non-human animals, e.g., rodents, e.g., mice or rats. However, the PD of such therapeutic molecules cannot properly be determined in certain non-human animals because these therapeutic molecules do not target the endogenous IL-4 or IL-4Rα proteins.

Moreover, the evaluation of therapeutic efficacy of human-specific IL-4 and IL-4Rα protein antagonists using various non-human animal models of diseases associated with abnormal Th2 cells is problematic in non-human animals in which such species-specific antagonists do not interact with the endogenous IL-4 or IL-4Rα proteins.

Accordingly, there is a need for non-human animals, e.g., rodents, e.g., murine animals, e.g., mice or rats, in which the IL-4 and/or IL-4Rα genes of the non-human animal are humanized in whole or in part or replaced (e.g., at the endogenous non-human loci) with human IL-4 and/or IL-4Rα genes comprising sequences encoding human or humanized IL-4 and/or IL-4Rα proteins, respectively.

There is also a need for non-human animals comprising IL-4 and/or IL-4Rα genes (e.g., humanized, or human) in which the IL-4 and/or IL-4R genes are under control of non-human regulatory elements (e.g., endogenous regulatory elements).

There is also a need for humanized non-human animals that express human or humanized IL-4 protein in blood, plasma or serum at a concentration similar to that of IL-4 protein present in blood, plasma or serum of an age-matched non-human animal that expresses functional IL-4 protein, but does not comprise the human or humanized IL-4 genes, and/or express human or humanized IL-4Rα protein on immune cells, e.g., B and T cells, at a level similar to that of IL-4Rα protein on immune cells, e.g., B and T cells, of an age-matched non-human animal that expresses functional IL-4Rα protein, but does not comprise the human or humanized IL-4Rα gene.

SUMMARY

Non-human animals comprising nucleic acid sequences encoding an IL-4 and/or an IL-4Rα protein that comprise a human sequence are provided.

Transgenic non-human animals comprising an IL-4 and/or an IL-4Rα gene that is human in whole or in part are provided.

Non-human animals that express human or humanized IL-4 and/or IL-4Rα proteins are provided.

Non-human animals having a replacement (in whole or in part) of endogenous non-human animal IL-4 and/or IL-4Rα genes are provided.

Non-human animals comprising an IL-4 and/or an IL-4Rα humanization (in whole or in part) at an endogenous non-human IL-4 and/or IL-4Rα loci are provided.

Non-human animals are provided that have a human or humanized IL-4 gene, wherein the non-human animals do not express endogenous IL-4 protein, and wherein the non-human animals express human or humanized IL-4 protein in blood, plasma or serum at a concentration similar to that of IL-4 protein present in blood, plasma or serum of an age-matched non-human animal that expresses functional endogenous IL-4 protein, but does not comprise the human or humanized IL-4 gene.

Non-human animals are provided that have a human or humanized IL-4Rα gene, wherein the non-human animals do not express endogenous IL-4Rα protein, and express human or humanized IL-4Rα protein on immune cells, e.g., B and T cells, at a level similar to that of IL-4Rα protein present on immune cells, e.g., B and T cells, of an age-matched non-human animal that expresses functional endogenous IL-4Rα protein, but does not comprise the human or humanized IL-4Rα gene.

In one aspect, non-human animals comprising a human or humanized IL-4 and/or IL-4Rα nucleic acid sequence are provided.

In one aspect, genetically modified non-human animals are provided that comprise a replacement at an endogenous IL-4 and/or IL-4Rα locus of a gene encoding an endogenous IL-4 and/or IL-4Rα with a gene encoding a human or humanized IL-4 and/or IL-4Rα protein. Rodents, e.g., mice or rats, are provided that comprise a replacement of an endogenous IL-4 gene, at an endogenous rodent IL-4 locus, with a human IL-4 gene, and/or comprise a replacement of an endogenous IL-4Rα gene, at an endogenous rodent IL-4Rα locus, with a human IL-4Rα gene. In one embodiment, the rodent is a mouse. In one embodiment, the rodent is a rat.

In one aspect, genetically modified rodents, e.g., mice or rats, are provided comprising a humanization of an endogenous rodent IL-4 gene, wherein the humanization comprises a replacement at an endogenous rodent IL-4 locus of a rodent nucleic acid comprising at least one exon of a rodent IL-4 gene with a nucleic acid sequence comprising at least one exon of a human IL-4 gene to form a modified IL-4 gene, wherein expression of the modified IL-4 gene is under control of rodent regulatory elements at the endogenous rodent IL-4 locus.

In one embodiment, the rodent is a mouse or a rat. In one embodiment, the rodent is a mouse. In one embodiment, the rodent is a rat.

In one embodiment, the modified IL-4 gene encodes human or humanized IL-4 protein and comprises exon 1 starting from the ATG initiation codon through exon 4 of the human IL-4 gene.

In one embodiment, the rodent is a mouse that is incapable of expressing a mouse IL-4 protein.

In one embodiment, the rodent is a mouse that expresses a mouse IL-4Rα protein encoded by an endogenous mouse IL-4Rα gene.

In one embodiment, the rodent is mouse that expresses a human or humanized IL-4Rα protein.

In one embodiment, the humanized IL-4Rα protein comprises the ectodomain of a human IL-4Rα protein.

In one embodiment, the humanized IL-4Rα protein comprises the transmembrane domain and cytoplasmic domain of a mouse IL-4Rα protein.

In one embodiment, the rodent is a mouse that comprises a replacement at an endogenous mouse IL-4Rα locus of a mouse nucleic acid comprising at least one exon of a mouse IL-4Rα gene with a nucleic acid sequence comprising at least one exon of a human IL-4Rα gene to form a modified IL-4Rα gene, wherein expression of the modified IL-4Rα gene is under control of mouse regulatory elements at the endogenous mouse IL-4Rα locus.

In one embodiment, the rodent is a mouse, wherein a contiguous genomic fragment of mouse IL-4 sequence comprising exon 1 starting from the ATG initiation codon through exon 4 of mouse IL-4 is replaced with a contiguous genomic fragment of human IL-4 sequence comprising exon 1 starting from the ATG initiation codon through exon 4 of human IL-4.

In one embodiment, expression of the modified IL-4Rα gene encoding the human or humanized IL-4Rα protein is under control of mouse regulatory elements at the endogenous mouse IL-4Rα locus.

In one aspect, genetically modified rodents, e.g., mice or rats, are provided comprising a humanization of an endogenous rodent IL-4Rα gene, wherein the humanization comprises a replacement at an endogenous rodent IL-4Rα locus of a rodent nucleic acid comprising an exon of a rodent IL-4Rα gene with a nucleic acid sequence encoding at least one exon of a human IL-4Rα gene to form a modified (i.e., humanized) IL-4Rα gene, wherein expression of the modified, humanized IL-4Rα gene is under control of rodent regulatory elements at the endogenous rodent IL-4Rα locus.

In one embodiment, the rodent is a mouse or a rat. In one embodiment, the rodent is a mouse. In one embodiment, the rodent is a rat.

In one embodiment, the modified IL-4Rα gene encodes human or humanized IL-4Rα protein and comprises exon 1 starting from the ATG initiation codon through exon 5 of the human IL-4Rα gene.

In one embodiment, the rodent is a mouse that is incapable of expressing a mouse IL-4Rα protein.

In one embodiment, the rodent is a mouse that expresses a mouse IL-4 protein encoded by an endogenous mouse IL-4 gene.

In one embodiment, the rodent is mouse that expresses a human or humanized IL-4 protein.

In one embodiment, the rodent is a mouse that comprises a replacement at an endogenous mouse IL-4 locus of a mouse nucleic acid comprising an exon of a mouse IL-4 gene with a nucleic acid sequence encoding at least one exon of a human IL-4 gene to form a modified IL-4 gene, wherein expression of the modified IL-4 gene is under control of mouse regulatory elements at the endogenous mouse IL-4 locus.

In one embodiment, the rodent is a mouse, and wherein a contiguous genomic fragment of mouse IL-4Rα sequence comprising exon 1 starting from the ATG initiation codon through exon 5 of IL-4Rα is replaced with a contiguous genomic fragment of human IL-4Rα sequence comprising exon 1 starting from the ATG initiation codon through exon 5 of human IL-4Rα.

In one aspect, genetically modified rodents, e.g., a mouse or rat, are provided that express a human or humanized IL-4 protein, wherein the rodent that expresses a human or humanized IL-4 protein comprises a normal immune system, i.e., the number of immune cells, e.g., B and T cells, in the blood, plasma or serum of the rodent expressing human or humanized IL-4 protein are similar to the number of immune cells, e.g., B and T cells, in the blood, plasma or serum of a rodent that expresses functional endogenous IL-4 protein. In one embodiment, the rodent is a mouse. In one embodiment, the rodent is a rat.

In one aspect, genetically modified rodents, e.g., a mouse or rat, are provided that express IL-4 protein from a human or humanized IL-4 gene, wherein the rodent expresses human or humanized IL-4 protein in its serum. In one embodiment, the rodent is a mouse. In one embodiment, the rodent is a rat.

In one embodiment, the serum of the rodent that expresses a human or humanized IL-4 protein has approximately the same level of IL-4 protein as a rodent that expresses a functional, endogenous IL-4 protein, e.g., a wild-type mouse or rat. In one embodiment, the rodent is a mouse. In one embodiment, the rodent is a rat.

In one embodiment, the mouse expresses human or humanized IL-4 protein in serum at a concentration of at least about 10%, 20%, 30%, 40%, 50%, 60%, 70%, 80%, 90%, 100%, 110%, 120%, 130%, 140%, 150%, 160%, 170%, 180%, 190% or 200% of the level of IL-4 protein present in the serum of an age-matched mouse that expresses functional endogenous IL-4 protein, but does not comprise a replacement of an endogenous IL-4 gene, at an endogenous mouse IL-4 locus, with a human IL-4 gene.

In one embodiment, the mouse expresses human or humanized IL-4 protein in serum at a concentration of between about 10% and about 200%, between about 20% and about 150%, or between about 30% and about 100% of the level of mouse IL-4 protein present in the serum of an age-matched mouse that expresses functional endogenous IL-4 protein, but does not comprise a replacement of an endogenous IL-4 gene, at an endogenous mouse IL-4 locus, with a human IL-4 gene.

In one aspect, genetically modified rodents, e.g., a mouse or rat, are provided that express a human or humanized IL-4Rα protein, wherein the rodent expresses a human or humanized IL-4Rα protein on immune cells, e.g., B and T cells, at a level similar to that of IL-4Rα protein present on immune cells, e.g., B and T cells, of an age-matched rodent that expresses functional endogenous IL-4Rα protein. In one embodiment, the rodent is a mouse. In one embodiment, the rodent is a rat.

In one aspect, genetically modified rodents, e.g., a mouse or rat, are provided that express IL-4Rα protein from a human IL-4Rα gene, wherein the rodent expresses human or humanized IL-4Rα protein on immune cells, e.g., B and T cells. In one embodiment, the rodent is a mouse. In one embodiment, the rodent is a rat.

In one embodiment, the immune cells, e.g., B and T cells, of the rodent that expresses a human or humanized IL-4Rα protein have approximately the same level of IL-4Rα protein on immune cells, e.g., B and T cells, of a rodent that expresses a functional, endogenous IL-4Rα protein, e.g., a wild-type mouse or rat. In one embodiment, the rodent is a mouse. In one embodiment, the rodent is a rat.

In one embodiment, the mouse expresses human or humanized IL-4Rα protein on immune cells, e.g., B and T cells, at an amount of at least about 10%, 20%, 30%, 40%, 50%, 60%, 70%, 80%, 90%, 100%, 110%, 120%, 130%, 140%, 150%, 160%, 170%, 180%, 190% or 200% of the amount of IL-4Rα protein on immune cells, e.g., B and T cells, of an age-matched mouse that expresses functional endogenous IL-4Rα protein, but does not comprise a replacement of an endogenous IL-4Rα gene, at an endogenous mouse IL-4Rα locus, with a human IL-4Rα gene.

In one embodiment, the mouse expresses human or humanized IL-4Rα protein on immune cells, e.g., B and T cells, at an amount of between about 10% and about 200%, between about 20% and about 150%, or between about 30% and about 100% of the amount of mouse IL-4Rα protein present on immune cells, e.g., B and T cells, of an age-matched mouse that expresses functional endogenous IL-4Rα protein, but does not comprise a replacement of an endogenous IL-4Rα gene, at an endogenous mouse IL-4Rα locus, with a human IL-4Rα gene.

In one aspect, a genetically modified rodent is provided, comprising a humanized IL-4Rα gene comprising a replacement of rodent IL-4Rα ectodomain-encoding sequence with human IL-4Rα ectodomain-coding sequence, wherein the humanized IL-4Rα gene comprises a rodent IL-4Rα transmembrane sequence and a rodent IL-4Rα cytoplasmic sequence, wherein the humanized IL-4Rα gene is under control of endogenous rodent IL-4Rα regulatory elements at the endogenous IL-4Rα locus, and wherein the rodent further comprises a humanized IL-4 gene encoding a human or humanized IL-4 protein, wherein the humanized IL-4 gene is under control of endogenous rodent IL-4 regulatory elements at the endogenous IL-4 locus.

In one embodiment, the rodent is a mouse or a rat. In one embodiment, the rodent is a mouse. In one embodiment, the rodent is a rat.

In one embodiment, the mouse is incapable of expressing a mouse IL-4 protein and incapable of expressing a mouse IL-4Rα protein.

In one embodiment, the rodent regulatory elements or sequences at the endogenous rodent IL-4 locus and/or rodent IL-4Rα locus are from a mouse or a rat.

In one embodiment, the rodent regulatory elements or sequences are endogenous rodent regulatory elements or sequences at the rodent IL-4 locus and/or rodent IL-4Rα locus.

In one aspect, a non-human animal, e.g., a rodent, e.g., a mouse or rat, is provided that expresses human or humanized IL-4 and/or IL-4Rα proteins, wherein the non-human animal expresses human or humanized IL-4 and/or IL-4Rα proteins from an endogenous non-human IL-4Rα locus and/or an endogenous non-human IL-4Rα locus. In an embodiment, the non-human animal is a rodent. In an embodiment, the rodent is a mouse. In an embodiment, the rodent is a rat.

In one aspect, a genetically modified mouse is provided that expresses human or humanized IL-4 protein from an endogenous mouse IL-4 locus, wherein the endogenous mouse IL-4 gene has been replaced, in whole or in part, with a human IL-4 gene.

In one embodiment, a contiguous mouse genomic nucleic acid of about 6.3 kb at an endogenous mouse IL-4 locus, including exon 1 starting from the ATG initiation codon through exon 4 (including the 3' untranslated region) and a portion of the 3' region downstream of exon 4, is deleted and replaced with about 8.8 kb of a human IL-4 nucleic acid sequence comprising exon 1 starting from the ATG initiation codon through exon 4 (including the 3' untranslated region) and a portion of the 3' region downstream of exon 4 of the human IL-4 gene. In a specific embodiment, the human IL-4 nucleic acid sequence replacing the mouse genomic nucleic acid comprises exon 1 starting from the ATG initiation codon through exon 4 and a portion of the 3' region downstream of exon 4 of the human IL-4 gene of human BAC RP11-17K19. In a specific embodiment, the modified IL-4 gene comprises mouse IL-4 5' regulatory elements and human IL-4 exon 1 starting from the ATG initiation codon through exon 4, i.e., the IL-4 protein coding sequences.

In one aspect, a genetically modified mouse is provided that comprises a nucleotide sequence encoding a human or humanized IL-4 protein, wherein the nucleotide sequence encoding the human or humanized IL-4 protein replaces, in whole or in part, an endogenous nucleotide sequence encoding an endogenous mouse IL-4 protein.

In one aspect, a genetically modified mouse is provided that expresses human or humanized IL-4Rα protein from an endogenous mouse IL-4Rα locus, wherein the endogenous mouse IL-4Rα gene has been replaced, in whole or in part, with a human IL-4Rα gene.

In one embodiment, a contiguous mouse genomic nucleic acid of about 7.1 kb at the endogenous mouse IL-4Rα locus, including exon 1 starting from the ATG initiation codon through exon 5 and a portion of intron 5, is deleted and replaced with about 15.6 kb of human IL-4Rα nucleic acid sequence comprising exon 1 starting from the ATG initiation codon through exon 5 and a portion of intron 5 of the human IL-4Rα gene. In a specific embodiment, the human IL-4α nucleic acid replacing the mouse genomic nucleic acid comprises exon 1 starting from the ATG initiation codon through exon 5 and a portion of intron 5 of the human IL-4α gene of human BAC RP11-16E24. In a specific embodiment, the human IL-4Rα nucleic acid replacing the mouse genomic nucleic acid comprises the entire human IL-4Rα ectodomain coding sequence.

In one aspect, a method is provided for making a humanized IL-4 rodent, comprising replacing a rodent IL-4 gene sequence encoding rodent IL-4 protein with a human IL-4 nucleic acid sequence comprising one or more exons of the human IL-4 gene sequence to form a modified, humanized IL-4 gene encoding human or humanized IL-4 protein, wherein the replacement is at an endogenous rodent IL-4 locus and the humanized IL-4 gene sequence comprising one or more exons of the human IL-4 gene sequence and encoding human or humanized IL-4 protein is operably linked to rodent regulatory elements or sequences (e.g., 5' and/or 3' regulatory elements) at the endogenous rodent IL-4 locus.

In one embodiment, the rodent is a mouse or a rat. In one embodiment, the rodent is a mouse. In one embodiment, the rodent is a rat.

In one embodiment, the rodent regulatory elements or sequences are derived from a mouse. In one embodiment, the rodent regulatory elements or sequences are derived from a rat.

In one embodiment, the rodent regulatory elements or sequences are endogenous rodent regulatory elements or sequences at the rodent IL-4 locus. In one embodiment, the rodent is a mouse. In one embodiment, the rodent is a rat.

In one embodiment, the human IL-4 nucleic acid sequence replacing the rodent IL-4 gene sequence comprises at least one exon of the human IL-4 gene sequence. In other embodiments, the human IL-4 nucleic acid sequence replacing the rodent IL-4 gene sequence comprises at least 2 or at least 3 exons of the human IL-4 gene sequence. In one embodiment, the human IL-4 nucleic acid sequence replacing the rodent IL-4 gene sequence comprises all 4 exons of the human IL-4 gene sequence. In one embodiment, the rodent is a mouse. In one embodiment, the rodent is a rat.

In one embodiment, the human IL-4 nucleic acid sequence replacing the rodent IL-4 gene sequence encodes a protein that is about 85%, 90%, 95%, 96%, 97%, 98%, or about 99% identical to a human IL-4 (e.g., the human IL-4 protein encoded by the nucleic acid set forth in GenBank Accession No. NM_000589.3s).

In one embodiment, the replacement is at an endogenous rodent IL-4 locus and the humanized IL-4 gene sequence comprising one or more exons of the human IL-4 gene sequence and encoding human or humanized IL-4 protein is operably linked to endogenous rodent regulatory elements or sequences (e.g., 5' and/or 3' regulatory elements) at the endogenous rodent IL-4 locus.

In one aspect, a method is provided for making a humanized IL-4 mouse, comprising replacing a mouse IL-4 gene sequence encoding mouse IL-4 protein with a human IL-4 gene sequence to form a modified, humanized IL-4 gene encoding human or humanized IL-4 protein.

In one embodiment, the replacement is at an endogenous mouse IL-4 locus, and the resulting humanized IL-4 gene encoding human or humanized IL-4 protein is operably linked to mouse regulatory elements or sequences (e.g., 5' and/or 3' regulatory elements) at the endogenous mouse IL-4 locus.

In one embodiment, the replacement is at an endogenous mouse IL-4 locus, and the humanized IL-4 gene encoding human or humanized IL-4 protein is operably linked to endogenous mouse regulatory elements or sequences (e.g., 5' and/or 3' regulatory elements) at the endogenous mouse IL-4 locus.

In one aspect, a method is provided for making a humanized IL-4Rα rodent, comprising replacing a rodent IL-4Rα gene sequence encoding rodent IL-4Rα protein with a human IL-4Rα nucleic acid sequence comprising one or more exons of the human IL-4Rα gene sequence to form a modified, humanized IL-4Rα gene encoding human or humanized IL-4Rα protein, wherein the replacement is at an endogenous rodent IL-4Rα locus and the humanized IL-4Rα gene sequence comprising one or more exons of the human IL-4Rα gene sequence and encoding human or humanized IL-4Rα protein is operably linked to rodent regulatory elements or sequences (e.g., 5' and/or 3' regulatory elements) at the endogenous rodent IL-4Rα locus.

In one embodiment, the rodent is a mouse or a rat. In one embodiment, the rodent is a mouse. In one embodiment, the rodent is a rat.

In one embodiment, the rodent regulatory elements or sequences are derived from a mouse. In one embodiment, the rodent regulatory elements or sequences are derived from a rat.

In one embodiment, the rodent regulatory elements or sequences are endogenous rodent regulatory elements or sequences at the rodent IL-4Rα locus. In one embodiment, the rodent is a mouse. In one embodiment, the rodent is a rat.

In one embodiment, the human IL-4Rα nucleic acid sequence replacing the rodent IL-4Rα gene sequence comprises at least one exon of the human IL-4Rα gene sequence. In other embodiments, the human IL-4Rα nucleic sequence replacing the rodent IL-4Rα gene sequence comprises at least 2, 3, 4, 5, 6, 7, or 8 exons of the human IL-4Rα gene sequence. In one embodiment, the human IL-4Rα nucleic sequence replacing the rodent IL-4Rα gene sequence comprises all 9 exons of the human IL-4Rα gene sequence. In one embodiment, the rodent is a mouse. In one embodiment, the rodent is a rat.

In one embodiment, the human IL-4Rα nucleic sequence replacing the rodent IL-4Rα gene sequence encodes a protein that is about 85%, 90%, 95%, 96%, 97%, 98%, or about 99% identical to a human IL-4Rα (e.g., the human IL-4Rα protein encoded by the nucleic acid set forth in GenBank Accession No. NM_000418.3).

In one embodiment, the human IL-4Rα nucleic acid sequence replacing the rodent IL-4Rα gene sequence comprises at least one exon of the human IL-4Rα gene sequence encoding the ectodomain of the human IL-4Rα protein. In other embodiments, the human IL-4Rα nucleic acid sequence replacing the rodent IL-4Rα gene sequence comprises at least 2, 3, or 4 exons of the human IL-4Rα gene sequence encoding the ectodomain of the human IL-4Rα protein. In one embodiment, the human IL-4Rα nucleic acid sequence replacing the rodent IL-4Rα gene sequence comprises all 5 exons of the human IL-4Rα gene sequence encoding the ectodomain of the human IL-4Rα protein. In one embodiment, the rodent is a mouse. In one embodiment, the rodent is a rat.

In one embodiment, the human or humanized IL-4Rα gene sequence replacing the rodent IL-4Rα gene sequence encodes an ectodomain of the IL-4Rα protein that is about 85%, 90%, 95%, 96%, 97%, 98%, or about 99% identical to the ectodomain of a human IL-4Rα protein (e.g., the human IL-4Rα protein encoded by the nucleic acid set forth in GenBank Accession No. NM_000418.3).

In one embodiment, the replacement is at an endogenous rodent IL-4Rα locus and the humanized IL-4Rα gene sequence comprising one or more exons of the human IL-4Rα gene sequence and encoding human or humanized IL-4Rα protein is operably linked endogenous rodent regulatory elements or sequences (e.g., 5' and/or 3' regulatory elements) at the endogenous rodent IL-4Rα locus.

In one aspect, a method is provided for making a humanized IL-4Rα mouse, comprising replacing a mouse IL-4Rα gene sequence encoding mouse IL-4Rα protein with a human IL-4Rα nucleic acid sequence to form a humanized IL-4Rα gene encoding human or humanized IL-4Rα protein.

In one embodiment, the replacement is at an endogenous mouse IL-4Rα locus, and the humanized IL-4Rα gene encoding human or humanized IL-4Rα protein is operably linked to mouse regulatory elements or sequences (e.g., 5' and/or 3' regulatory elements) at the endogenous mouse IL-4Rα locus.

In one embodiment, the replacement is at an endogenous mouse IL-4Rα locus, and the humanized IL-4Rα gene encoding human or humanized IL-4Rα protein is operably linked to endogenous mouse regulatory elements or sequences (e.g., 5' and/or 3' regulatory elements) at the endogenous mouse IL-4Rα locus.

In various aspects, the genetically modified non-human animals, e.g., rodents, e.g., mice or rats, described herein comprise the genetic modifications in their germ-line.

In one aspect, a non-human animal, e.g., rodent, e.g., a mouse or rat, embryo comprising a genetic modification as described herein is provided.

In one aspect, a non-human animal, e.g., rodent, e.g. a mouse or rat, host embryo is provided that comprises a donor cell that comprises a genetic modification as described herein.

In one aspect, a pluripotent or totipotent non-human animal, e.g., rodent, e.g., mouse or rat, cell comprising a genetic modification as described herein is provided. In one embodiment, the cell is a rodent cell. In one embodiment, the cell is a mouse cell. In one embodiment, the cell is a rodent ES cell. In one embodiment, the cell is a mouse ES cell.

In one aspect, a non-human animal, e.g., rodent, e.g., mouse or rat, egg is provided, wherein the non-human animal egg comprises an ectopic non-human animal chromosome, wherein the ectopic non-human animal chromosome comprises a genetic modification as described herein. In one embodiment, the non-human animal is a rodent. In one embodiment, the rodent is a mouse. In one embodiment, the rodent is a rat.

In one aspect, the mouse embryo, egg, or cell that is genetically modified to comprise a human IL-4 gene or human IL-4Rα gene is of a mouse that is of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. In one embodiment, the mouse is Swiss or Swiss Webster mouse.

In various aspects, the non-human animals comprising a human or humanized IL-4R and/or IL-4 nucleic acid sequence are selected from mammals and birds. In one embodiment, the non-human animals are mammals. In one embodiment, the mammals are murine.

In one aspect, a method of screening for a human-specific IL-4 or IL-4Rα antagonist is provided. The method is useful for identifying therapeutic candidates and evaluating therapeutic efficacy. The method comprises administering an agent to a genetically modified rodent that is doubly humanized for IL-4 and IL-4Rα as described herein, determining an effect of the agent on a biological function mediated by the IL-4/IL-4Rα signaling pathway, and identifying the agent as a human-specific IL-4 or IL-4Rα antagonist if it antagonizes the function mediated by the IL-4/IL-4Rα signaling pathway in the genetically modified rodent.

In one embodiment, the agent comprises an immunoglobulin variable domain that binds IL-4 or IL-4Rα. In one embodiment, the agent specifically binds human IL-4 or IL-4Rα, but not rodent IL-4 or IL-4Rα. In one embodiment, the agent is an antibody. In a specific embodiment, the agent is an antibody that specifically binds human IL-4Rα, but not rodent IL-4Rα.

In one embodiment, the screening method utilizes a doubly humanized mouse that expresses a human IL-4 protein, and a humanized IL-4Rα protein, wherein the humanized IL-4Rα protein includes the ectodomain of a human IL-4Rα protein, linked to the transmembrane and cytoplasmic domains of the endogenous mouse IL-4Rα protein, and wherein the mouse does not express murine IL-4 or murine IL-4Rα.

In some embodiments, the method of screening includes the steps of inducing in a doubly humanized rodent as described herein a disease associated with IL-4/IL-4Rα signaling, administering an agent to the rodent, determining whether the agent ameliorates the disease, and identifying the agent as a human-specific IL-4 or IL-4Rα antagonist suitable for treating the disease if the agent ameliorates the disease.

In some embodiments, the disease associated with IL-4/IL-4Rα signaling is airway inflammation, which can be induced in a rodent by intranasal administration of an allergen (e.g., house dust mite extract) in one or more doses for a period of time. The effect of an agent can be determined by measuring whether the extent of airway inflammation (reflected by e.g., mucus accumulation, infiltrating cells in bronchoalveolar lavage fluid, and/or levels of total circulating IgE), is reduced as a result of the administration of the agent.

In some embodiments, the disease associated with IL-4/IL-4Rα signaling is skin inflammation or atopic dermatitis, which can be induced in a rodent by creating skin injury and exposing the injured skin to an allergen (e.g., bacterial toxin or house dust mite extract) in one or more doses for a period of time. The effect of an agent can be determined by measuring whether skin inflammation is reduced as a result of the administration of the agent.

In a further aspect, a triply humanized non-human animal whose IL-4, IL-4Rα, and IL-33 genes have been humanized as described herein is used to evaluate the pharmacodynamics (PD) and therapeutic efficacy of a compound or a combination of compounds.

Each of the aspects and embodiments described herein are capable of being used together, unless excluded either explicitly or clearly from the context of the embodiment or aspect.

BRIEF DESCRIPTION OF THE DRAWINGS

FIG. 10A illustrates that the mouse IL-33 gene (top) spanning the coding region from exon 2 starting at the ATG initiation codon through the stop codon in exon 8 is deleted and replaced by the coding region from exon 2 starting at the ATG codon through exon 8 (including the 3' untranslated region) of the human IL-33 gene (bottom). FIG. 10B shows the humanized IL-33 allele in mouse ES cell clone MAID 7060, which contains a loxP neomycin selection cassette. FIG. 10C shows the humanized IL-33 allele in mouse ES cell clone MAID 7061, in which the neomycin selection cassette has been deleted, with loxP and cloning sites (77 bp) remaining downstream of the human IL-33 sequence, and mouse 3' UTR retained downstream of the loxP site.

DETAILED DESCRIPTION

IL-4 and IL-4Rα as Therapeutic Targets

Allergic disorders are a spectrum of diseases that are occurring at an increasing rate, especially in developed countries. Atopic dermatitis, asthma, and allergic rhinitis are the most common inflammatory conditions among patients with allergies; these patients often suffer the onset of multiple clinical symptoms. The pathogenesis of allergy is linked to abnormal immune responses against exogenous antigens (see Mueller et al. (2002) Structure, binding, and antagonists in the IL-4/IL-13 receptor system, Biochim Biophys Acta 1592:237-250).

Over-production of antigen-specific IgE is an essential component to trigger allergic inflammation. Abnormal type-2 T helper cell (Th2) polarization contributes to the increased IgE responses.

Interleukin-4 (IL-4) and interleukin-13 (IL-13), originally identified from activated T cells, are major Th2 cytokines that play central roles in initiating and sustaining the immune and inflammatory reactions in allergies.

IL-4 and IL-13 signaling are mediated by two distinct receptor complexes with a shared subunit, IL-4 receptor alpha (IL-4Rα), which may contribute to the overlapping biological responses between these two cytokines. See FIG. 1.

Receptors for Interleukin-4/13 Signal Transduction and the Mechanism of Action of Dupilumab.

IL-4Rα forms two distinct heterodimeric receptor complexes to mediate the biological functions of IL-4 and IL-13 in a tissue- and response-specific manner. The type I receptor comprised of IL-4Rα and common cytokine receptor gamma chain (γC) is unique for IL-4. Type II receptor formed between IL-4Rα and IL-13Rα1 is the primary receptor for IL-13, but is also functional for IL-4. In addition, IL-13 will bind to a second high affinity receptor, IL-13Rα2, which is generally recognized as a decoy receptor or with a possible, pro-fibrotic effect in the full-length form.

Dupilumab is an antagonistic monoclonal antibody against human IL-4Rα that inhibits induced biological activities from IL-4 and IL-13. Dupilumab blocks IL-4 signal transduction by preventing its binding to receptor subunits, whereas the inhibitory effect on IL-13 signaling is likely mediated through interfering with the dimeric receptor interaction.

Dupilumab, a fully-human monoclonal antibody directed against the shared IL-4Rα subunit, was developed at Regeneron Pharmaceuticals, Inc. using VelocImmune® mice. Dupilumab is undergoing clinical trials for the treatment of moderate-to-severe asthma and for the treatment of moderate-to-severe atopic dermatitis.

Evaluating the potency of dupilumab in murine models presents multiple challenges: (a) dupilumab does not recognize the cognate mouse IL-4 receptor; and (b) there is a lack of functional interaction between mouse IL-4 protein and human IL-4 receptor.

IL-4 Gene and Protein

Figure 1:
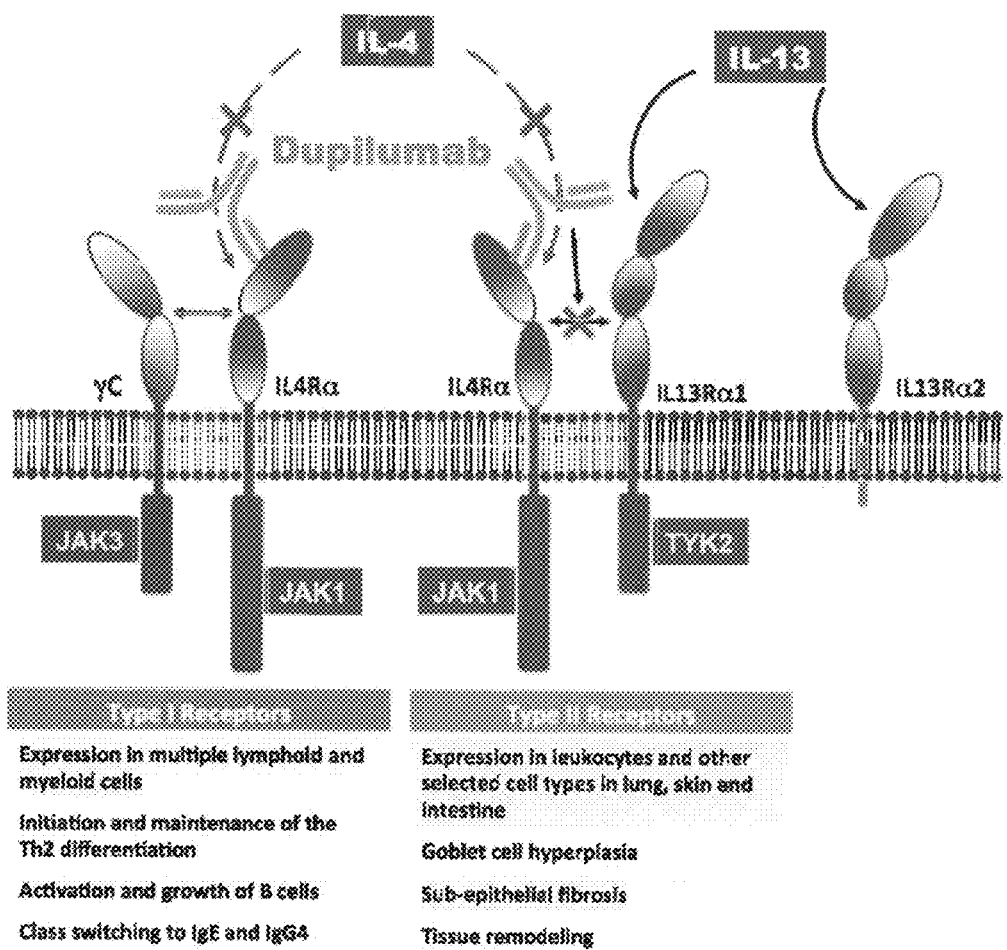
FIG. 1 provides an illustration, not to scale, of the receptors for IL-4 and IL-13 signal transduction and the mechanism of action of dupilumab, a neutralizing fully human monoclonal antibody that binds specifically to the human IL-4 receptor α chain (IL-4Rα).

The IL-4 gene encodes a secreted IL-4 protein, which plays an important role in the activation of B cells, as well as other cell types (see FIG. 1).

Human IL-4.

NCBI Gene ID: 3565; Primary source: HGNC:6014; RefSeq transcript: NM_000589.3; UniProt ID: P05112; Genomic assembly: GRCh37; Location: chr5:132,009,743-132,018,576+ strand.

The human IL-4 gene is located on chromosome 5, at 5q31.1. The human IL-4 gene has 4 exons and encodes a precursor polypeptide of 153 amino acids in length, including a 24 amino acid signal peptide, and a 129 amino acid mature IL-4 protein.

Mouse IL-4.

NCBI Gene ID: 16189; Primary source: MGI:96556; RefSeq transcript: NM_021283.2; UniProt ID: P07750; Genomic assembly: GRCm38; Location: chr11:53,612,350-53,618,606– strand.

The mouse IL-4 gene is located on chromosome 11, at 11 31.97 cM. The mouse IL-4 gene has 4 exons and encodes a precursor polypeptide of 140 amino acids in length, including a 20 amino acid signal peptide, and a 120 amino acid mature IL-4 protein.

IL-4Rα Gene and Protein

The IL-4Rα gene encodes the transmembrane receptor IL-4Rα protein, which is expressed primarily on B and T cells, is a receptor for the IL-4 and IL-13 proteins (see FIG. 1).

Human IL-4Rα.

NCBI Gene ID: 3566; Primary source: MGI:6015; RefSeq transcript: NM_000418.3; UniProt ID: P24394; Genomic assembly: GRCh37; Location: chr16:27,351,525-27,367,111+ strand.

The human IL-4Rα gene is located on chromosome 16 at 16p12.1-p11.2. The human IL-4Rα gene has 9 coding exons and encodes a precursor polypeptide of 825 amino acids, including a 25 amino acid signal peptide, and an 800 amino acid mature IL-4Rα protein, with the first 207 amino acid residues of the mature protein constituting the extracellular domain. The extracellular domain (i.e., ectodomain) of the human IL-4Rα protein is encoded by coding exons 1 through 5 of the human IL-4Rα gene.

Mouse IL-4Rα.

NCBI Gene ID: 16190; Primary source: MGI:105367; RefSeq transcript: NM_001008700.3; UniProt ID: P16382; Genomic assembly: GRCm38; Location: chr11:125,565,655-125,572,745+ strand.

The mouse IL-4Rα gene is located on chromosome 7 at 7 68.94 cM. The mouse IL-4Rα gene has 9 coding exons and encodes a precursor polypeptide of 810 amino acids, including a 25 amino acid signal peptide, and a 785 amino acid mature IL-4Rα protein, with the first 208 amino acid residues of the mature protein constituting the extracellular domain. The extracellular domain (i.e., ectodomain) of the mouse IL-4Rα protein is encoded by coding exons 1 through 5 of the mouse IL-4Rα gene.

Species Specificity of IL-4 and IL-4Rα Proteins

As shown herein, mouse, but not human, IL-4 is functional in wild-type mice, and, conversely, human, but not mouse, IL-4 is functional in humanized IL-4Rα (Il4ra$^{hu/hu}$) mice. (See also, e.g., Andrews et al. (2001) Reconstitution of a functional human type II IL-4/IL-13 receptor in mouse B cells: demonstration of species specificity, J Immunol. 166: 1716-1722).

Species Specificity of Human IL-4 and IL-4Rα Inhibitors

Candidate therapeutic molecules that target the IL-4 or IL-4Rα proteins are typically evaluated for pharmacokinetics (PK) and pharmacodynamics (PD) in non-human animals, e.g., rodents, e.g., mice or rats. Such therapeutic molecules are also tested for in vivo therapeutic efficacy in non-human animal, e.g., rodent, e.g., mouse or rat, models of human diseases, disorders and conditions associated with abnormal Th2 cells.

However, therapeutic molecules that are specific for the human IL-4 or IL-4Rα proteins, e.g., human-specific IL-4 or IL-4Rα inhibitors, cannot be adequately evaluated for PD or in vivo therapeutic efficacy in rodents, in particular mice, because the targets of these therapeutic molecules are missing. This problem is not overcome using transgenic non-human animals, e.g., rodents, e.g., mice or rats, expressing human IL-4 or IL-4Rα proteins because of the above-mentioned species specificity of IL-4 protein.

Accordingly, in various embodiments, to assess the PD and in vivo therapeutic efficacy of a human-specific IL-4 or IL-4Rα protein antagonist or inhibitor in non-human animals, e.g., rodents, e.g., mice or rats, it is desirable to replace the endogenous IL-4 and/or IL-4Rα proteins with human IL-4 and/or IL-4Rα proteins.

Further, in various embodiments, in order to avoid potential problems of over- or under-expression of the human IL-4 and/or IL-4Rα proteins, it is desirable to insert the human IL-4 and/or IL-4Rα genes into the genome of the non-human animals, e.g., rodents, e.g., mice or rats, at the endogenous IL-4 and/or IL-4Rα gene loci, and to express the human IL-4 and/or IL-4Rα proteins in non-human animals, e.g., rodents, e.g., mice or rats, under the control, at least in part, of the endogenous IL-4 and/or IL-4Rα regulatory elements.

Genetically Modified Non-Human Animals

Genetically modified non-human animals are provided herein whose endogenous IL-4 gene and/or IL-4Rα gene has been replaced in whole or in part, at an endogenous IL-4 locus and/or the IL-4Rα locus, with a human IL-4 nucleic acid and/or human IL-4Rα nucleic acid to form a modified IL-4 gene and/or modified IL-4Rα gene which encodes a human or humanized IL-4 and/or human or humanized IL-4Rα protein.

The phrase "non-human animal" as used herein refers to any vertebrate organism that is not a human. In some embodiments, the non-human animal is a mammal. In specific embodiments, the non-human animal is a rodent such as a rat or a mouse.

In one aspect, genetically modified rodents, e.g., mice or rats, are provided whose endogenous rodent IL-4 gene has been replaced in whole or in part, at an endogenous IL-4 locus, with a human IL-4 nucleic acid.

The replacement involves a replacement of at least one exon, i.e., one or more exons, of a rodent IL-4 gene with a human nucleic acid comprising at least one exon of a human IL-4 gene. In some embodiments, a contiguous rodent genomic fragment which includes exon 1 starting from the ATG initiation codon through exon 4 of a rodent IL-4 gene has been replaced with a contiguous human genomic fragment including exon 1 starting from the ATG initiation codon through exon 4 of a human IL-4 gene. In a specific embodiment, the rodent is a mouse, and a contiguous mouse genomic fragment of about 6.3 kb at an endogenous mouse IL-4 locus, including exon 1 starting from the ATG initiation codon through exon 4 (including the 3' untranslated region) and a portion of the 3' region downstream of exon 4, is deleted and replaced with about 8.8 kb of a human IL-4 nucleic acid sequence comprising exon 1 starting from the ATG initiation codon through exon 4 (including the 3' untranslated region) and a portion of the 3' region downstream of exon 4 of the human IL-4 gene.

In some embodiments, the replacement results in a modified, humanized IL-4 gene at an endogenous IL-4 gene locus, wherein the expression of the modified IL-4 gene is under control of the endogenous regulatory elements at the endogenous IL-4 locus. The term "regulatory elements" as used herein refer to transcriptional regulatory sequences, including both 5' transcriptional regulatory sequences such as promoter, enhancer, and suppressor elements, and 3' transcriptional regulatory sequences such as a transcriptional termination sequence. In some embodiments, the expression of a modified IL-4 gene is under control of the endogenous 5' regulatory elements. In other embodiments, the expression of a modified IL-4 gene is under control of the endogenous 3' regulatory elements. In certain embodiments, the expression of a modified IL-4 gene is under control of the endogenous 5' and 3' regulatory elements.

The modified, humanized IL-4 gene formed at an endogenous IL-4 locus encodes a human or humanized IL-4 protein. The term "humanized" refer to nucleic acids or proteins which include portions or sequences of a gene or protein found in a non-human animal (e.g., a rodent such as mouse or rat), and also include portions or sequences that differ from those found in a non-human animal but instead correspond to (identical with) portions or sequences of the counterpart human gene or protein. The modified, humanized IL-4 gene can encode an IL-4 protein that is at least 85%, 90%, 95%, 96%, 97%, 98%, or 99% identical, or is 100% identical, with a human IL-4 protein (e.g., the human IL-4 protein encoded by the nucleic acid set forth in GenBank Accession No. NM_000589.3).

A genetically modified rodent having a replacement of an endogenous rodent IL-4 gene in whole or in part, at an endogenous IL-4 locus, with a human IL-4 nucleic acid, can be homozygous or heterozygous with respect to the replacement. In some embodiments, the genetically modified rodent is heterozygous with respect to the replacement, i.e., only one of the two copies of the endogenous rodent IL-4 gene has been replaced with a human IL-4 nucleic acid. In other embodiments, the genetically modified rodent is homozygous with respect to the replacement, i.e., both copies of the endogenous rodent IL-4 gene have been replaced with a human IL-4 nucleic acid.

The genetically modified rodent expresses a human or humanized IL-4 protein in the serum. In some embodiments, the genetically modified rodent does not express endogenous rodent IL-4 protein. In one embodiment, the serum of the rodent that expresses a human or humanized IL-4 protein has approximately the same level of IL-4 protein as a rodent that expresses a functional, endogenous IL-4 protein, e.g., a wild-type rodent (e.g., a rodent that expresses functional endogenous IL-4 protein, but does not comprise a replacement of an endogenous IL-4 gene in whole or in part, at an endogenous IL-4 locus, with a human IL-4 nucleic acid). By "approximately the same level" it is meant a level that falls within 25%, 20%, 15%, 10%, 5% or less in either direction (i.e., greater than or less than) of the level in a wild-type rodent. In other embodiments, the rodent expresses a human or humanized IL-4 protein in serum at a concentration of at least about 10%, 20%, 30%, 40%, 50%, 60%, 70%, 80%, 90%, 100%, 110%, 120%, 130%, 140%, 150%, 160%, 170%, 180%, 190% or 200% of the level of IL-4 protein present in the serum of an age-matched rodent that expresses functional endogenous IL-4 protein, but does not comprise a replacement of an endogenous IL-4 gene in whole or in part, at an endogenous IL-4 locus, with a human IL-4 nucleic acid.

In some embodiments, a genetically modified rodent having a replacement of an endogenous rodent IL-4 gene in whole or in part with a human IL-4 nucleic acid and expressing a human or humanized IL-4 protein in the serum has a normal immune system, i.e., the number of immune cells, e.g., B and T cells, in the blood, plasma or serum of the rodent expressing human or humanized IL-4 protein are similar to the number of immune cells, e.g., B and T cells, in the blood, plasma or serum of a rodent that expresses functional endogenous IL-4 protein and does not have a replacement of an endogenous rodent IL-4 gene in whole or in part with a human IL-4 nucleic acid.

In additional embodiments, a genetically modified rodent having a replacement of an endogenous rodent IL-4 gene in whole or in part with a human IL-4 nucleic acid and expressing a human or humanized IL-4 protein, also includes a replacement of the endogenous rodent IL-4Rα gene in whole or in part, at an endogenous IL-4Rα locus, with a human IL-4Rα nucleic acid, and as a result, also expresses a human or humanized IL-4Rα protein.

In another aspect, genetically modified rodents, e.g., mice or rats, are provided whose endogenous rodent IL-4Rα gene has been replaced in whole or in part, at an endogenous IL-4Rα locus, with a human IL-4Rα nucleic acid.

The replacement involves replacement of at least one exon, i.e., one or more exons, of a rodent IL-4Rα gene with a human nucleic acid comprising at least one exon of a human IL-4Rα gene. In some embodiments, the replacement involves replacement of at least one of the exons of a rodent IL-4Rα gene encoding the rodent ectodomain with at least one of the exons of human IL-4Rα gene encoding the human ectodomain. In some embodiments, the replacement involves replacement with a human nucleic acid comprising at least 2, 3 or 4 of the 5 exons encoding the ectodomain of a human IL-4Rα gene. In other embodiments, a contiguous rodent genomic fragment which includes exon 1 starting from the ATG initiation codon through exon 5 of a rodent IL-4Rα gene has been replaced with a genomic fragment including exon 1 starting from the ATG initiation codon through exon 5 of a human IL-4Rα gene. In a specific embodiment, the rodent is a mouse, and a contiguous mouse genomic fragment of about 7.1 kb at an endogenous mouse IL-4Rα locus, including exon 1 starting from the ATG initiation codon through exon 5 and a portion of intron 5, is deleted and replaced with about 15.6 kb of a human IL-4Rα nucleic acid sequence comprising exon 1 starting from the ATG initiation codon through exon 5 and a portion of intron 5 of the human IL-4Rα gene.

In some embodiments, the replacement results in a modified, humanized IL-4Rα gene at an endogenous IL-4Rα gene locus, wherein the expression of the modified IL-4Rα gene is under control of the endogenous regulatory elements at the endogenous IL-4Rα locus.

The modified, humanized IL-4Rα gene formed at an endogenous IL-4Rα locus encodes a human or humanized IL-4Rα protein. In some embodiments, the modified, humanized IL-4Rα gene encodes an IL-4Rα protein that is at least 85%, 90%, 95%, 96%, 97%, 98%, or 99% identical, or is 100% identical, with a human IL-4Rα protein (e.g., the human IL-4 Ra protein encoded by the nucleic acid set forth in GenBank Accession No. NM_000418.3). In other embodiments, the modified IL-4Rα gene encodes a humanized IL-4Rα protein which comprises an ectodomain that is at least 85%, 90%, 95%, 96%, 97%, 98%, or 99% identical, or is 100% identical, with the ectodomain of a human IL-4Rα protein (e.g., the human IL-4Rα protein encoded by the nucleic acid set forth in GenBank Accession No. NM_000418.3). In specific embodiments, the transmembrane and cytoplasmic domains of the humanized IL-4Rα protein are identical with the transmembrane and cytoplasmic domains of the endogenous rodent IL-4Rα protein.

A genetically modified rodent having a replacement of an endogenous rodent IL-4Rα gene in whole or in part, at an endogenous IL-4Rα locus, with a human IL-4Rα nucleic acid, can be homozygous or heterozygous with respect to the replacement. In some embodiments, the genetically modified rodent is heterozygous with respect to the replacement, i.e., only one of the two copies of the endogenous rodent IL-4Rα gene has been replaced with a human IL-4Rα nucleic acid. In other embodiments, a genetically modified rodent is homozygous with respect to the replacement, i.e., both copies of the endogenous rodent IL-4Rα gene have been replaced with a human IL-4Rα nucleic acid.

The genetically modified rodent disclosed herein expresses a human or humanized IL-4Rα protein on immune cells, e.g., B and T cells. In some embodiments, the genetically modified rodent does not express endogenous rodent IL-4Rα protein. In one embodiment, the immune cells of the rodent that expresses a human or humanized IL-4Rα protein have approximately the same level of IL-4Rα protein on immune cells as a rodent that expresses a functional, endogenous IL-4Rα protein on immune cells of a wild-type rodent that expresses a functional, endogenous IL-4Rα protein and does not express the human or humanized IL-4Rα protein. In other embodiments, the rodent expresses human or humanized IL-4Rα protein on immune cells at an amount of at least about 10%, 20%, 30%, 40%, 50%, 60%, 70%, 80%, 90%, 100%, 110%, 120%, 130%, 140%, 150%, 160%, 170%, 180%, 190% or 200% of the amount of IL-4Rα protein present on immune cells of an age-matched rodent that expresses functional endogenous IL-4Rα protein, but does not comprise a replacement of an endogenous IL-4Rα gene in whole or in part with a human IL-4Rα nucleic acid.

In some embodiments, a genetically modified rodent having a replacement of an endogenous rodent IL-4Rα gene in whole or in part with a human IL-4Rα nucleic acid and expressing a human or humanized IL-4Rα protein has a normal immune system, i.e., the number of immune cells, e.g., B and T cells, in the blood, plasma or serum of the rodent expressing human or humanized IL-4Rα protein are similar to the number of immune cells, e.g., B and T cells, in the blood, plasma or serum of a wild-type rodent (e.g., a rodent that expresses functional endogenous IL-4Rα protein and does not have a replacement of an endogenous rodent IL-4Rα gene in whole or in part with a human IL-4Rα nucleic acid).

In some embodiments, a genetically modified rodent having a replacement of an endogenous rodent IL-4Rα gene in whole or in part with a human IL-4Rα nucleic acid and expressing a human or humanized IL-4Rα protein is capable of and functional in mediating IL-4 dependent signaling and IL-13 dependent signaling. For example, a humanized IL-4Rα protein having the ectodomain of a human IL-4Rα protein, expressed on immune cells of a genetically modified rodent, interacts with human IL-4 and mediates human IL-4 dependent signaling via forming Type I receptor (see FIG. 1). Such humanized IL-4Rα protein having the ectodomain of a human IL-4Rα protein also interacts with human and mouse IL-13, and mediates IL-13 dependent signaling via forming Type II receptor (see FIG. 1). The functionality of a humanized IL-4Rα protein expressed in a genetically modified rodent can be evaluated in various assays known in the art, including those specifically described in the examples hereinbelow, such as an assay that measures IL-4 induced IgE class switching using primary B cells derived from a genetically modified rodent.

In additional embodiments, a genetically modified rodent having a replacement of an endogenous rodent IL-4Rα gene in whole or in part with a human IL-4Rα nucleic acid and expressing a human or humanized IL-4Rα protein, also includes a replacement of the endogenous rodent IL-4 gene in whole or in part, at an endogenous IL-4 locus, with a human IL-4 nucleic acid, and as a result, also expresses a human or humanized IL-4.

In a further aspect, doubly humanized rodents, e.g., mice or rats, are provided whose endogenous rodent IL-4 gene has been replaced in whole or in part, at an endogenous IL-4 locus, with a human IL-4 nucleic acid, and whose endogenous rodent IL-4Rα gene has also been replaced in whole or in part, at an endogenous IL-4Rα locus, with a human IL-4Rα nucleic acid. Such doubly humanized rodents can be homozygous or heterozygous with respect to each humanization replacement. In a specific embodiment, the doubly humanized rodent is homozygous with respect to both humanized IL-4 and humanized IL-4Rα.

The genetic modification to an endogenous rodent IL-4 gene in a doubly humanized rodent includes those modifications or replacements described hereinabove for a genetically modified rodent having a replacement of an endogenous rodent IL-4 gene in whole or in part with a human IL-4 nucleic acid. Similarly, the genetic modification to an endogenous rodent IL-4Rα gene in a doubly humanized rodent includes those modifications or replacements described hereinabove for a genetically modified rodent having a replacement of an endogenous rodent IL-4Rα gene in whole or in part with a human IL-4Rα nucleic acid. Thus, the features disclosed hereinabove with respect to humanization of the rodent IL-4 gene and with respect to humanization of the rodent gene, respectively, are incorporated herein specifically for a doubly humanized rodent.

In specific embodiments, a doubly humanized rodent, e.g., a mouse or rat, is provided that expresses a human IL-4 protein and a humanized IL-4Rα protein, wherein the humanized IL-4Rα protein includes the ectodomain of a human IL-4Rα protein and includes the transmembrane and cytoplasmic domains of the rodent's endogenous IL-4Rα protein. In particular embodiments, the expression of the human IL-4 protein and the humanized IL-4Rα protein are under control of the endogenous rodent regulatory sequences at the endogenous rodent IL-4 locus and rodent IL-4Rα locus, respectively.

In some embodiments, a doubly humanized rodent has a normal immune system (i.e., the number of immune cells is approximately the same as a wild-type rodent), has approximately the same level of IL-4 protein in the serum, and expresses approximately the same amount of IL-4Rα protein on immune cells, as a wild-type rodent, a wild-type rodent being a rodent that expresses functional, endogenous IL-4 protein and IL-4Rα protein and does not express human or humanized IL-4 protein or IL-4Rα protein.

In particular embodiments, a doubly humanized rodent exhibits a functional IL-4 signaling pathway. By "functional IL-4 signaling pathway" it is meant that both a human or humanized IL-4 protein, and a human or humanized IL-4Rα protein, are expressed in a doubly humanized rodent and interact with each other in the doubly humanized rodent so as to effectively mediate downstream signal transduction and carry out the biological activities of a normal IL-4 signaling pathway. The biological activities of a normal IL-4 signaling pathway are described hereinabove and illustrated in FIG. 1, including those mediated through Type I receptor such as initiation and maintenance of the Th2 differentiation, activation and grown of B cells, class switching to IgE and IgG4, and those mediated through Type II receptor signaling such as Goblet cell hyperplasia, sub-epithelial fibrosis, and tissue remodeling. For example, a functional IL-4 signaling pathway in a doubly humanized rodent is reflected by an inflammatory phenotype characterized by, e.g., increased IgE in circulation, airway inflammation and/or eosinophilic infiltrating cells in response to a house dust mite challenge, which phenotype is also observed in wild-type rodents without the double humanization.

Methods of Making a Genetically Modified Non-Human Animal

A genetically modified non-human animal such as a rodent can be made using methods known in the art. For example, a targeting vector can be made that contains a human nucleic acid (such as a human IL-4 or IL-4Rα gene, in whole or in part), flanked by non-human animal homologous upstream and downstream regions. The targeting construct can also contain a drug selection cassette (e.g., a floxed hygro selection cassette, which can be subsequently removed by a transient Cre-expression vector), which is positioned 3' to the human nucleic acid. The targeting vector can be introduced into the genome of a non-human animal cell, e.g., an embryonic stem (ES) cell (such as a mouse ES cell) by electroporation, for example. Correctly targeted ES cell clones can then be introduced into an early stage embryo (e.g., 8-cell stage mouse embryo). Non-human animals fully derived from correctly targeted ES cells are identified based on, for example, allele analysis. For non-human animals where suitable genetically modifiable ES cells are not readily available, other methods can be employed to make a non-human animal comprising genetic modifications as described herein. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

Methods of Employing a Genetically Modified Non-Human Animal

In one aspect, genetically modified IL-4 and/or IL-4Rα non-human animals disclosed herein are used for evaluating the pharmacodynamics (PD) and therapeutic efficacy of human-specific IL-4 and/or IL-4Rα antagonists, e.g., neutralizing anti-IL-4 and/or anti-IL-4Rα antibodies (e.g., dupilumab) in various disease models, as further illustrated in the examples below.

In some embodiments, the present invention provides a method of screening for human-specific IL-4 or IL-4Rα antagonists using a doubly humanized IL-4 and IL-4Rα mice disclosed herein.

By "IL-4 or IL-4Rα antagonists" it is meant molecules (e.g., antibodies) that block, suppress or inhibit one or more biological functions mediated by IL-4 or IL-4Rα. "Human-specific IL-4 or IL-4Rα antagonists" refer to antagonists that are specific to the human IL-4 or IL-4Rα, and substantially do not act on rodent IL-4 or IL-4Rα.

In specific embodiments, the method of screening utilizes a doubly humanized mouse that expresses a human IL-4 protein, and a humanized IL-4Rα protein, wherein the humanized IL-4Rα protein includes the ectodomain of a human IL-4Rα protein, linked to the transmembrane and cytoplasmic domains of the endogenous mouse IL-4Rα protein, and wherein the mouse does not express mouse IL-4 or mouse IL-4Rα.

In some embodiments, the method of screening for a human-specific IL-4 or IL-4Rα antagonist comprises administering an agent to a genetically modified rodent that is doubly humanized for IL-4 and IL-4Rα as described herein, determining an effect of the agent on a biological function mediated by the IL-4/IL-4Rα signaling pathway, and identifying the agent as a human-specific IL-4 or IL-4Rα antagonist if it antagonizes the function mediated by the IL-4/IL-4Rα signaling pathway in the genetically modified rodent.

In one embodiment, the agent comprises an immunoglobulin variable domain that binds IL-4 or IL-4Rα. In one embodiment, the agent specifically binds human IL-4 or IL-4Rα, but not rodent IL-4 or IL-4Rα. In one embodiment, the agent is an antibody. In a specific embodiment, the agent is an antibody that specifically binds human IL-4Rα, but not rodent IL-4Rα.

In one embodiment, the method of screening utilizes a doubly humanized mouse that expresses a human IL-4 protein, and a humanized IL-4Rα protein, wherein the humanized IL-4Rα protein includes the ectodomain of a human IL-4Rα protein, linked to the transmembrane and cytoplasmic domains of the endogenous mouse IL-4Rα protein, and wherein the mouse does not express murine IL-4 or murine IL-4Rα.

In some embodiments, the method of screening includes the steps of inducing in a doubly humanized rodent as described herein a disease associated with IL-4/IL-4Rα signaling, administering an agent to the rodent, determining whether the agent ameliorates the disease, and identifying the agent as a human-specific IL-4 or IL-4Rα antagonist suitable for treating the disease if the agent ameliorates the disease.

By "disease associated with IL-4/IL-4Rα signaling" it is meant a disease in which the biological function mediated by IL-4/IL-4Rα signaling is implicated. Examples of diseases associated with IL-4/IL-4Rα signaling include, e.g., inflammatory diseases or disorders, such as asthma, atopic dermatitis, chronic obstructive pulmonary disease (COPD) (which may result at least in part from cigarette smoke), inflammatory bowel disease, multiple sclerosis, arthritis, allergic rhinitis, eosinophilic esophagitis and psoriasis. Asthma can be eosinophilic or non-eosinophilic asthma, and steroid sensitive or steroid resistant asthma.

In some embodiments, the disease associated with IL-4/IL-4Rα signaling is airway inflammation, which can be induced in a rodent by intranasal administration of an allergen (e.g., house dust mite extract) in one or more doses for a period of time. The effect of an agent can be determined by measuring whether the extent of airway inflammation (reflected by e.g., mucus accumulation, eosinophilic infiltrating cells in bronchoalveolar lavage fluid, levels of total circulating IgE, and/or alteration in expression profile measurable by microarray expression analysis) is reduced as a result of the administration of the agent. The allergen used for inducing airway inflammation and the agent being tested can be administered simultaneously or at different times. In some embodiments, the allergen is given to the rodent in one or more doses, and the agent being tested is administered to the rodent after at least one dose of the allergen has been given to the rodent.

In some embodiments, the disease associated with IL-4/IL-4Rα signaling is skin inflammation or atopic dermatitis, which can be induced in a rodent by creating skin injury and exposing the injured skin to an allergen (e.g., bacterial toxin or house dust mite extract) in one or more doses for a period of time. The effect of an agent can be determined by measuring whether skin inflammation is reduced as a result of administration of the agent.

In a further aspect, triply humanized non-human animals, i.e., non-human animals whose IL-4, IL-4Rα, and IL-33 genes have been humanized, are used to evaluate the pharmacodynamics (PD) and therapeutic efficacy of candidate compounds such as, e.g., human-specific IL-4 and/or IL-4Rα antagonists, and human-specific IL-33 antagonists.

By "IL-33 antagonists" it is meant molecules (e.g., antibodies) that block, suppress or inhibit one or more biological functions or signaling mediated by IL-33. "Human-specific IL-33 antagonists" refer to antagonists that are specific to the human IL-33, and substantially do not act on rodent IL-33. IL-33 is known to stimulate signal transduction through ST2 and IL-1 RAcP, which is diminished in the presence of an antagonist, such as an IL-33 antibody. Inhibition of IL-33 signal transduction through ST2 and IL-1 RAcP can be determined by assaying for IL-33 signal transduction in an in vitro or in vivo assay, such as those described in US Published Application 2014/0271658 A1, the entire contents of which are incorporated herein by reference. For example, an assay such as that described in US Published Application 2014/0271658 A1 can be used to assess the effect of an antibody to IL-33 on lung inflammation in allergen-sensitized animals that are homozygous for expression of human IL-33. An IL-33 antibody that is effective as an IL-33 antagonist should demonstrate a trend towards reduction in inflammatory cells in the lung, as well as a trend towards reduction in cytokines such as IL-4 and IL-5.

In specific embodiments, a triply humanized non-human animal is used herein to evaluate candidate compounds, wherein the triply humanized animal is a triply humanized mouse that expresses a human IL-4 protein, a humanized IL-4Rα protein which includes the ectodomain of a human IL-4Rα protein linked to the transmembrane and cytoplasmic domains of a mouse IL-4Rα protein, and a human IL-33 protein, wherein the mouse does not express mouse IL-4, mouse IL-4Rα or mouse IL-33.

In some embodiments, a triply humanized non-human animal is used to evaluate the pharmacodynamics (PD) and therapeutic efficacy of a candidate compound, such as, e.g., a human-specific IL-4 and/or IL-4Rα antagonist, or a human-specific IL-33 antagonist. For example, a human-specific IL-4 antibody, a human-specific IL-4Rα antibody, and a human-specific IL-33 antibody, can be tested individually in a triply humanized animal (such as a rodent, e.g., mouse or rat), and their PD profiles and therapeutic efficacies can be evaluated and compared.

In other embodiments, a triply humanized non-human animal is used to evaluate the efficacy of a combination of compounds, e.g., a combination of a human specific IL-4 and/or IL-4Rα antagonist antibody, with a human-specific IL-33 antagonist antibody, as compared to the efficacy of the compounds when used individually to determine, for example, whether the combination of compounds exhibits a synergistic therapeutic effect. In specific embodiments, a combination of a human specific IL-4 antibody and a human-specific IL-33 antibody are tested in a triply humanized non-human animal. In other specific embodiments, a combination of a human specific IL-4Rα antibody and a human-specific IL-33 antibody are tested in a triply humanized non-human animal.

To evaluate a candidate compound or a combination of compounds, a disease associated with the IL-4/IL-4Rα signaling and the IL-33 signaling can be induced in the triply humanized animal. Examples of diseases associated with the IL-4/IL-4Rα signaling and the IL-33 signaling include, e.g., inflammatory diseases or disorders, such as asthma, atopic dermatitis, chronic obstructive pulmonary disease (COPD) (which may result at least in part from cigarette smoke), inflammatory bowel disease, multiple sclerosis, arthritis, allergic rhinitis, eosinophilic esophagitis and psoriasis. Asthma can be eosinophilic or non-eosinophilic asthma, and steroid sensitive or steroid resistant asthma. The effect of a compound or a combination of compounds can be assessed similarly to an IL-4/IL-4Rα doubly humanized animal as described hereinabove.

The present invention is further illustrated by the following, non-limiting examples.

Example 1

Replacement of the Endogenous Mouse IL-4 Gene with a Human IL-4 Gene

Figure 2A:
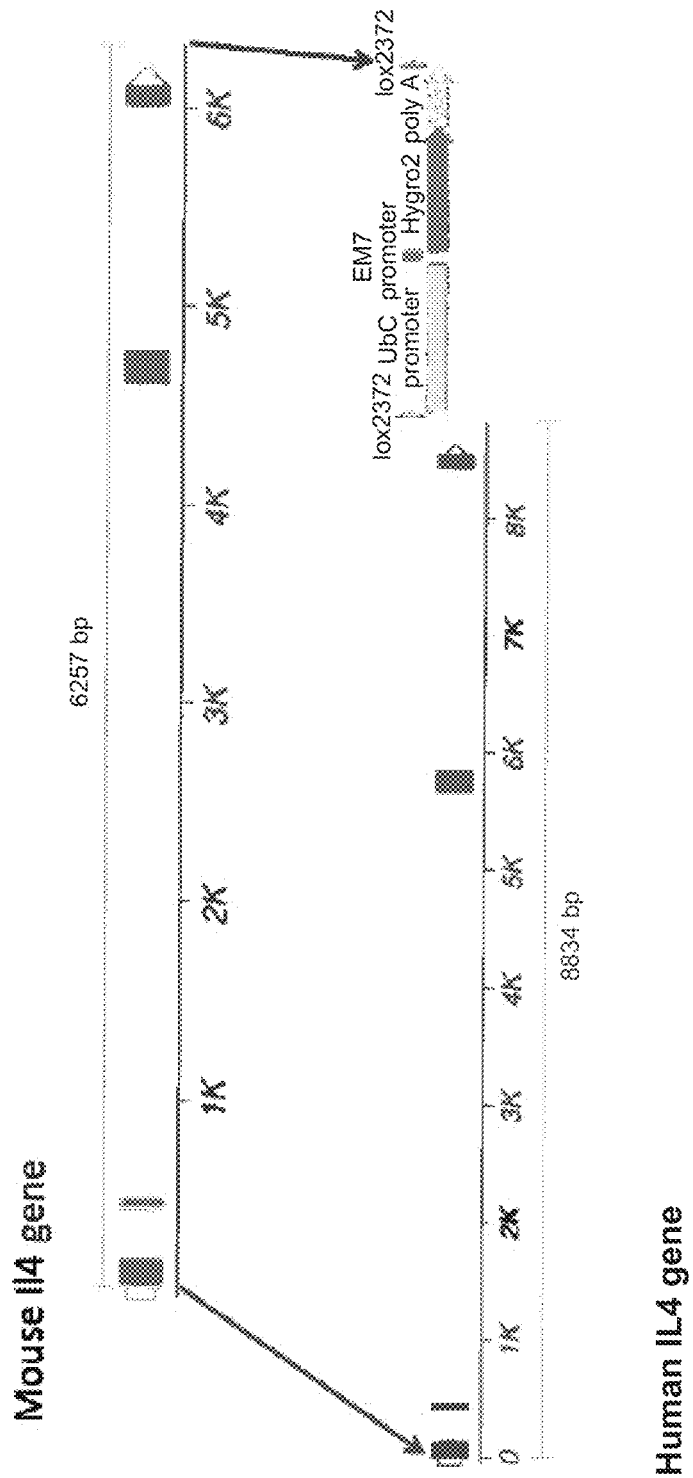
FIGS. 2A-2B provide an illustration, not to scale, of the strategies for humanization of the IL-4 (Il4) and IL-4Rα (Il4ra) loci. (2A) The mouse IL-4 gene (top) spanning the coding region from exon 1 starting at the ATG initiation codon through exon 4 (including the 3' untranslated region) and a portion of the 3' region downstream of exon 4 are deleted and replaced by the coding region from exon 1 starting at the ATG codon through exon 4 (including the 3' untranslated region) and a portion of the 3' region downstream of exon 4 of the human IL-4 gene (bottom) along with a floxed hygro selection cassette loxP, as indicated. (2B) The mouse IL-4Rα gene (top) spanning the coding region from exon 1 starting from the ATG initiation codon through exon 5 and a portion of intron 5 are deleted and replaced by the coding region from exon 1 starting from the ATG initiation coding through exon 5 and a portion of intron 5 of the human IL-4Rα gene (bottom) and a floxed neo selection cassette, as indicated.

The 8.8 kb human IL-4 gene containing the coding portion of exon 1 starting from the ATG initiation codon through exon 4 (including the 3' untranslated region) and a portion of the 3' region downstream of exon 4 of the human IL-4 gene replaced 6.3 kb of the murine IL-4 gene locus spanning the coding portion of exon 1 starting from the ATG initiation codon through exon 4 (including the 3' untranslated region) and a portion of the 3' region downstream of exon 4. See FIG. 2A.

A targeting construct for replacing the mouse with the human IL-4 gene in a single targeting step was constructed using VelociGene® genetic engineering technology (see Valenzuela et al. (2003) High-throughput engineering of the mouse genome coupled with high-resolution expression analysis, Nature Biotech, 21(6):652-659). Mouse and human IL-4 DNA were obtained from bacterial artificial chromosome (BAC) clones bMQ-41A12 and RP11-17K19, respectively. Briefly, an SbfI linearized targeting construct generated by gap repair cloning containing mouse IL-4 upstream and downstream homology arms flanking a 8.8 kb human IL-4 sequence extending from the ATG codon in exon 1 through exon 4 (including the 3' untranslated region) and a portion of the 3' region downstream of exon 4 (genomic coordinates: GRCh37: chr5:132,009,743-132,018,576 (+strand)) and a floxed hygro selection cassette, was electroporated into F1H4 mouse embryonic stem (ES) cells (C57BL/6×129 F1 hybrid). Correctly targeted ES cells (MAID 879) were further electroporated with a transient Cre-expressing vector to remove the drug selection cassette. Targeted ES cell clones without drug cassette (MAID 1553) were introduced into an 8-cell stage SW mouse embryo by the VelociMouse® method (see, U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses, Nature Biotech. 25(1):91-99). VelociMice® (F0 mice fully derived from the donor ES cell) bearing the humanized IL-4 gene were identified by genotyping for loss of mouse allele and gain of human allele using a modification of allele assay (see, Valenzuela et al. (2003)).

Correctly targeted ES cell clones were identified by a loss-of-native-allele (LONA) assay (Valenzuela et al. 2003) in which the number of copies of the native, unmodified IL-4 gene were determined by two TaqMan™ quantitative polymerase chain reactions (qPCRs) specific for sequences in the mouse IL-4 gene that were targeted for deletion. The qPCR assays comprised the following primer-probe sets (written 5' to 3'): upstream forward primer, CATGCACGGA GATGGATGTG (SEQ ID NO:1); upstream reverse primer, GACCCCTCAG GTCCACTTAC C (SEQ ID NO:2); upstream probe, FAM-AACGTCCTCA CAGCAACGA-MGB (SEQ ID NO:3); downstream forward primer, GTGCCCAGGT GTGCTCATG (SEQ ID NO:4); downstream reverse primer, CGCCTGCCTC CTCACTTTAT C (SEQ ID NO:5); downstream probe, FAM-ATCTGCTTCA CCATCCACT-MGB (SEQ ID NO:6); in which FAM refers to the 5-carboxyfluorescein fluorescent probe and BHQ refers to the fluorescence quencher of the black hole quencher type (Biosearch Technologies). DNA purified from ES cell clones that have taken up the targeting vector and incorporated in their genomes was combined with TaqMan™ Gene Expression Master Mix (Life Technologies) according to the manufacturer's suggestions in a 384-well PCR plate (MicroAmp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream IL-4-specific qPCRs and two qPCRs for non-targeted reference genes were run for each DNA sample. The differences in the Ct values (ΔCt) between each IL-4-specific qPCR and each reference gene qPCR were calculated, and then the difference between each ΔCt and the median ΔCt for all samples assayed was calculated to obtain ΔΔCt values for each sample. The copy number of the IL-4 gene in each sample was calculated from the following formula: copy number=2×2$^{-\Delta\Delta Ct}$. A correctly targeted clone, having lost one of its native copies, will have a IL-4 gene copy number equal to one. Confirmation that the human IL-4 gene sequence replaced the deleted mouse IL-4 gene sequence in the humanized allele was confirmed by a TaqMan™ qPCR assay that comprises the following primer-probe sets (written 5' to 3'): human forward primer, GCCTG-GACCA AGACTCTGT (SEQ ID NO:7); human reverse primer, ACCGTGGGAC GGCTTCTTAC (SEQ ID NO:8); human upstream probe, FAM-CACCGAGTTG ACCG-TAACAG ACATC-BHQ (SEQ ID NO:9). Confirmation that the hygro selection cassette was inserted with the human IL-4 gene sequence in the humanized allele was confirmed by a TaqMan™ qPCR assay that comprises the following primer-probe sets (written 5' to 3'): hygro forward primer, TGCGGCCGAT CTTAGCC (SEQ ID NO:10); hygro reverse primer, TTGACCGATT CCTTGCGG (SEQ ID NO:11); hygro probe, FAM-ACGAGCGGGT TCGGC-CCATT C-BHQ (SEQ ID NO:12).

The same LONA assay was used to assay DNA purified from tail biopsies for mice derived from the targeted ES cells to determine their IL-4 genotypes and confirm that the humanized IL-4 allele had transmitted through the germline. Two pups heterozygous for the replacement are bred to generate a mouse that is homozygous for the replacement of the endogenous mouse IL-4 gene by the human IL-4 gene. Pups that are homozygous for the replacement are used for phenotyping.

The upstream junction of the murine IL-4 locus and the sequence containing the human IL-4 gene is designed to be within 5'-TGCTGATTGG CCCAGAATAA CTGACAATCT GGTGTAATAA AATTTTCCAA TGTAAACTCA TTTTCCCTTG GTTTCAGCAA CTT-TAACTCT ATATATAGAG AGACCTCTGC CAGCATT-GCA TTGTTAGCAT CTCTTGATAA ACTTAATTGT CTCTGTCAC TGACGGCACA GAGCTATTG(A TGGGTCTCAC CTCCCAACTG CTTCCCCCTC TGT-TCTTCCT GCTAGCATGT GCCGGCAACT TTGTC-CACGG ACACAAGTGC GATATCACCT TACAGGA-GAT CATCAAAACT TTGAACAGCC TCACAGAGCA GMG)GTGAGT ACCTATCTGG CACCATCTCT CCA-GATGTTC TGGTGATGCT CTCAGTATTT CTAG-GCATGA AAACGTTAAC AGCTGCTAGA GAAGTTG-GAA CTGGTGGTTG GTGGCAGTCC AGGGCACACA GCGAGGCTTC TCCCCTGC (SEQ ID NO:13), wherein the human IL-4 sequences are italicized and the IL-4 coding sequences are bracketed. The downstream junction of the sequence containing the human IL-4 gene and the floxed hygro selection cassette is designed to be within 5'-TGTT-TATTTT GCAG(AATTCC TGTCCTGTGA AGGAAGC-CAA CCAGAGTACG TTGGAAAACT TCTTGGAAAG GCTAAAGACG ATCATGAGAG AGAAATATTC AAAGTGTTCG AGCTGA)ATAT TTTAATTTAT GAGTTTTTGA TAGCTTTATT TTTTAAGTAT TTATAT-ATTT ATAACTCATC ATAAAATAM GTATATATAG AATCTAACAG CAATGGCATT TAATGTATTG GCTAT-GTTTA CTTGACAAAT GAAATTATGG TTTGCAACTT TTAGGGAAAT CAATTTAGTT TACCMGAGA CTATAMTGC TATGGGAGCA AAACAGGAAA GAC-CACTTCC CCCTCGAGGG GTTCCCTCTC GAGT-TAGGGA CATAACACAC AAGATAATTA AAGAACA-CAA GGCCATACAA GATGCGGCCG CACCGGTATA ACTTCGTATA AGGTATCCTA TACGAAGTTA TATG-CATGGC CTCCGCCCG GGTTTTGGCG CCTC-CCGCGG GCGCCCCCCT CCTCACGGCG AGCGCT-GCCA CGTCAGACGA AGGGCGCAGC GAGCGTCCTG ATCCT (SEQ ID NO:14), wherein the human IL-4 sequences are italicized and the IL-4 coding sequences are bracketed. The downstream junction of the sequence of the floxed hygro selection cassette and the murine IL-4 locus is designed to be within 5'-TGC-CAAGTTC TAATTCCATC AGACCTCGAC CTGCAGC-CGG CGCGCCATAA CTTCGTATAA GGTATCCTAT ACGAAGTTAT CTCGAGAGGA GTTCCCACCC TTCT-CAAGAG CATAATGCGC AGATCATTAA GGGACA-GATG CAGGCTGGGG AGACGGTTCA GCAGTTAGGA GTACCTGTTG CTCTTCCAGA GGACCCAGGT TCAATTCCCG GCACTCACAT AGCAGCTTAA AACAATAACT CAAGTTCTGG GGGAGCTGAT GCTCTCCTCT GGCCTCCTGT GGAGGTACAC AGAC-CACATG CCTGTAGGCA AGACACCCAC ACA-CATAAAA ACAAAATAAA ATAAGGATAG AAAGGC-CAGG GGGATGAATC CAGAGGTAGA AGAAAACTTA TTCCCTGGAA TTGTCCTCTG ACTCCCCTCC CAAAACCTCT AACACGCAT (SEQ ID NO:15), wherein the hygro cassette sequences are italicized.

Example 2

Replacement of the Endogenous Mouse IL-4Rα Ectodomain Gene Sequence with a Human IL-4Rα Ectodomain Gene Sequence The 15.6 kb human IL-4Rα gene containing exon 1 starting from the ATG initiation codon through exon 5 and a portion of intron 5 of the human IL-4Rα gene replaced 7.1 kb of the murine IL-4Rα gene locus spanning coding exon 1 starting from the ATG initiation codon through exon 5 and a portion of intron 5. Mouse exons 6 through 9 were retained; only exons 1 through 5 (i.e., the ectodomain) were humanized. See FIG. 2B.

A targeting construct for replacing the mouse with the human IL-4Rα gene in a single targeting step was constructed using VelociGene® genetic engineering technology (see Valenzuela et al. (2003) High-throughput engineering of the mouse genome coupled with high-resolution expression analysis, Nature Biotech, 21(6):652-659). Mouse and human IL-4Rα DNA were obtained from bacterial artificial chromosome (BAC) clones RP23-136G14 and RP11-166E24, respectively. Briefly, a NotI linearized targeting construct generated by gap repair cloning containing mouse IL-4Rα gene upstream and downstream homology arms flanking a 15.6 kb human IL-4Rα sequence extending from the ATG codon in exon 1 through exon 5 and a portion of intron 5 (genomic coordinates: GRCh37: chr16:27,351,525-27,367,111 (+ strand)) and a floxed neo selection cassette, was electroporated into F1H4 mouse embryonic stem (ES) cells (C57BL/6×129 F1 hybrid). Correctly targeted ES cells (MAID 803) were further electroporated with a transient Cre-expressing vector to remove the drug selection cassette. Targeted ES cell clones without drug cassette (MAID 1444) were introduced into an 8-cell stage SW mouse embryo by the VelociMouse® method (see, U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses, Nature Biotech. 25(1):91-99). VelociMice® (F0 mice fully derived from the donor ES cell) bearing the humanized IL-4Rα gene were identified by genotyping for loss of mouse allele and gain of human allele using a modification of allele assay (see, Valenzuela et al. (2003)).

Correctly targeted ES cell clones were identified by a loss-of-native-allele (LONA) assay (Valenzuela et al. 2003) in which the number of copies of the native, unmodified IL-4Rα gene were determined by two TaqMan™ quantitative polymerase chain reactions (qPCRs) specific for sequences in the mouse IL-4Rα gene that were targeted for deletion. The qPCR assays comprised the following primer-probe sets (written 5' to 3'): upstream forward primer, CCGCTGGCAT GTGTATTGTG (SEQ ID NO:16); upstream reverse primer, TGAGTGTGGG ACCCTCAAGA G (SEQ ID NO:17); upstream probe, FAM-TGAC-CCAAGC CCTACATGGC CACT-BHQ (SEQ ID NO:18); downstream forward primer, TGAGGAGAGC TCACGGGAAT C (SEQ ID NO:19); downstream reverse primer, ACCCATCTCC TGCGTTTCTG (SEQ ID NO:20); downstream probe, FAM-TTGACACGCC AGCTACACTG CTCCA-BHQ (SEQ ID NO:21); in which FAM refers to the 5-carboxyfluorescein fluorescent probe and BHQ refers to the fluorescence quencher of the black hole quencher type (Biosearch Technologies). DNA purified from ES cell clones that have taken up the targeting vector and incorporated in their genomes was combined with TaqMan™ Gene Expression Master Mix (Life Technologies) according to the manufacturer's suggestions in a 384-well PCR plate (MicroAmp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream IL-4Rα-specific qPCRs and two qPCRs for non-targeted reference genes were run for each DNA sample. The differences in the Ct values (ΔCt) between each IL-4Rα-specific qPCR and each reference gene qPCR were calculated, and then the difference between each ΔCt and the median ΔCt for all samples assayed was calculated to obtain ΔΔCt values for each sample. The copy number of the IL-4Rα gene in each sample was calculated from the following formula: copy number=$2 \times 2^{-\Delta\Delta Ct}$. A correctly targeted clone, having lost one of its native copies, will have a IL-4Rα gene copy number equal to one. Confirmation that the human IL-4Rα gene sequence replaced the deleted mouse IL-4Rα gene sequence in the humanized allele was confirmed by a TaqMan™ qPCR assay that comprises the following primer-probe sets (written 5' to 3'): human forward primer, ACCTGCGTCT CCGACTACAT G (SEQ ID NO:22); human reverse primer, GAGCTCGGTG CTGCAATTG (SEQ ID NO:23); human probe, FAM-TGGGACCATT CATCTTCCAC TCGCA-BHQ (SEQ ID NO:24). Confirmation that the neo selection cassette was inserted with the human IL-4Rα gene sequence in the humanized allele was confirmed by a TaqMan™ qPCR assay that comprises the following primer-probe sets (written 5' to 3'): neo forward primer, GGTGGAGAGG CTATTCGGC (SEQ ID NO:25); neo reverse primer, GAACACGGCG GCATCAG (SEQ ID NO:26); neo probe, FAM-TGGGCACAAC AGACAATCGG CTG-BHQ (SEQ ID NO:27).

The same LONA assay was used to assay DNA purified from tail biopsies for mice derived from the targeted ES cells to determine their IL-4Rα genotypes and confirm that the humanized IL-4Rα allele had transmitted through the germline. Two pups heterozygous for the replacement are bred to generate a mouse that is homozygous for the replacement of the endogenous mouse IL-4Rα gene by the human IL-4Rα gene. Pups that are homozygous for the replacement are used for phenotyping.

The upstream junction of the murine IL-4Rα locus and the sequence containing the human IL-4Rα gene is designed to be within 5'-TGGGGGAGGG AGGCCATGAC ACAAATGAAA TGGACCCCGC TGACCAGGA TCA-GCATCTG CCCACTCTTC TTTCTGCAGG CAC-CTTTTGT GTCCCCA(ATG GGGTGGCTTT GCTCTGGGCT CCTGTTCCCT GTGAGCTGCC TGGTCCTGCT GCAGGTGGCA AGCTCTG)GTA AGT-CACCACT TCTCAATCAT TCATTTGTTG GCTAT-TAATG GCGTGCCAGG GTCCTGCAGT ATGTCACCTG GCC (SEQ ID NO:28), wherein the human IL-4Rα sequences are italicized and the IL-4Rα coding sequences are underlined. The downstream junction of the sequence containing the human IL-4Rα gene and the floxed neo selection cassette is designed to be within 5'-GTCA-GATCGT GGAGGGTCTC GGACGAGGG TCCTGAC-CCT GGGTCTCCAG TCCTGGGAAG TGGAGCCCAG GCTGTACCAT GGCTGACCTC AGCTCATGGC Tcccgggctc gataactata acggtcctaa ggtagcgact cgagataact tcg-tataatg tatgctatac gaagttatat gcatggcctc cgcgccgggt tttg-gcgcct cccgcgggcg cccccctcct cacggcgagc gctg (SEQ ID NO:29), wherein the human IL-4Rα sequences are italicized and the cassette sequences are in lower case. The downstream junction of the sequence of the floxed neo selection cassette and the murine IL-4Rα locus is designed to be within 5'-tattgttttg ccaagttcta attccatcag acctcgacct gcagc-ccta gataacttcg tataatgtat gctatacgaa gttatcctag gttggagctc TCTGTAGCCA GGTAACCAAG GGTCCCAGGG GAACCCCCAG TGTGGACGCG GACTGCACAT GACACAGGGC GGCCTCCCCA TTCATGACTG TTTTTCTCCT TGCAG(ACTTC CAGCTGCCCC TGA-TACAGCG CCTTCCACTG GGGGTCACCA TCTCCT-GCCT CTGCATCCCG TTGTTTTGCC TGTTCTGTTA CTTCAGCATT ACCAA)GTGAG TTCCTGCTTT GGCTGGTGTC TCTGGCTGGC CCTTCAGCAG TGCTCTCAGA GGTCACAGTC ATTGTGCTGG CTGAGAAAAG (SEQ ID NO:30), wherein the mouse IL-4Rα coding sequences are bracketed, and the neo cassette sequences are in lower case.

Example 3

Generation of Doubly Humanized IL-4/IL-4Rα Mice

The doubly humanized IL-4/IL-4Rα (Il4$^{hu/hu}$/Il4ra$^{hu/hu}$) mice were generated as follows. ES cell clone MAID 803, comprising the humanized IL-4Rα gene and floxed neo cassette, was electroporated with a Cre expression vector to remove the floxed neo cassette to generate ES cell clone MAID 1444, comprising the humanized IL-4Rα gene without a drug selection cassette (see Example 2). The same targeting construct that was used to generate ES cell clone MAID 879, comprising the humanized IL-4 gene and floxed hygro cassette (see Example 1), was electroporated into ES cell clone MAID 1444 to generate 879 Het/1444 Het (Il4$^{+/hu}$/Il4ra$^{+/hu}$) ES cells, which were subsequently electroporated with a Cre expression vector to remove the floxed hygro cassette to generate an ES cell clone (MAID 1553/1444) comprising humanized IL-4 and IL-4Rα genes. The ES cell clone MAID 1553/1444 without drug cassette was introduced into an 8-cell stage SW mouse embryo to generate doubly humanized IL-4/IL-4Rα mice.

Example 4

Figure 2B:
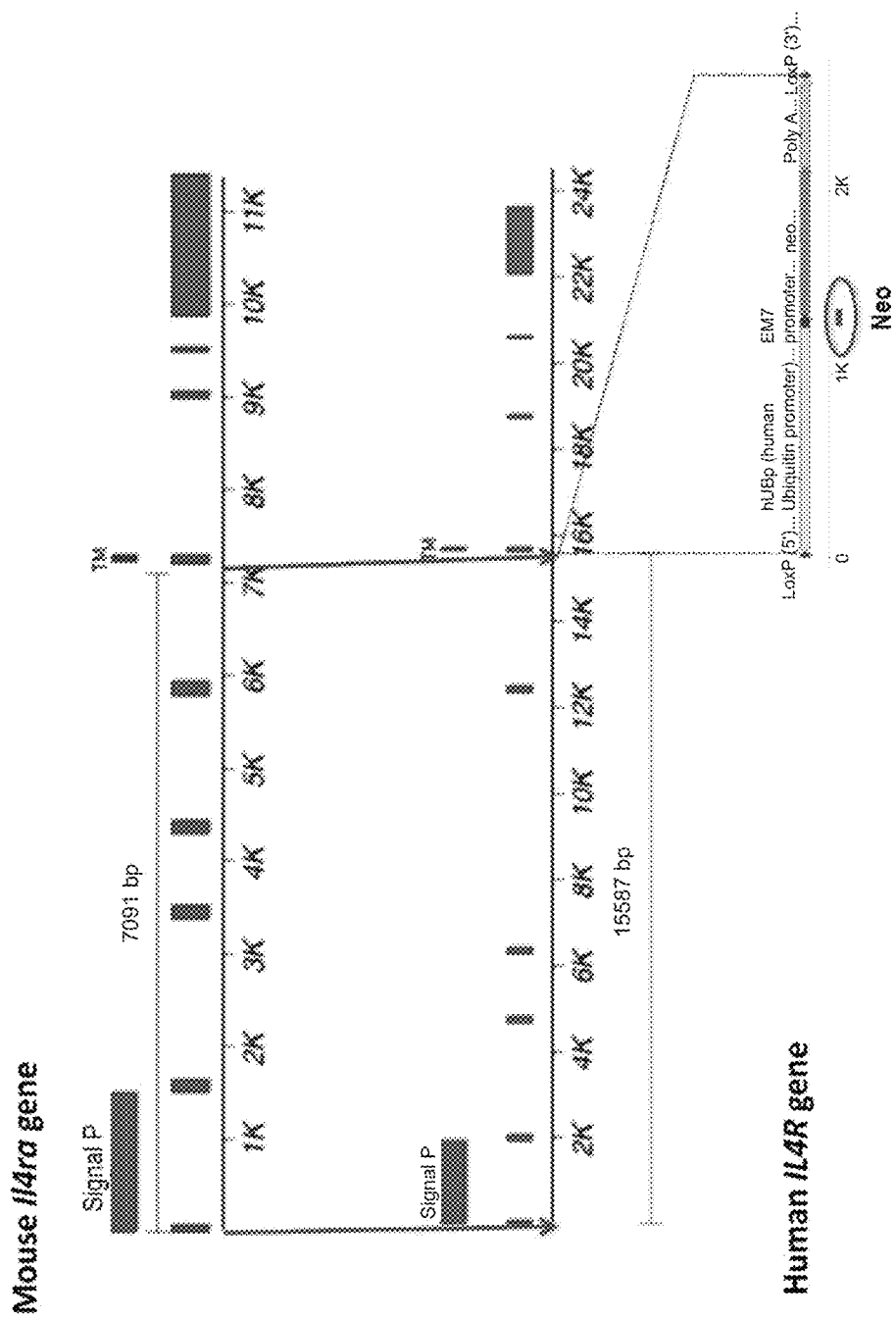

Efficacy Evaluation of Dupilumab, a Fully Human IL-4Rα mAb, in Mice with Human IL-4 and IL4Rα Gene Replacements Methods Genetically engineered mice were created using VelociGene® technology to replace both mouse full-length IL-4 locus with 8.8 kb of human IL-4 genomic sequences (see Example 1 and FIG. 2A) and the extracellular domain (i.e., ectodomain) of mouse IL-4Rα (CD124) gene with a 15.6 kb fragment of the corresponding human IL-4Rα genomic DNA (see Example 2 and FIG. 2B).

Mice with a homozygous humanized IL-4Rα gene were validated for expression and function of the human gene. To determine the expression of human IL-4Rα by humanized mice, splenocytes from wild-type and humanized mice were collected and processed for fluorescent activated cell sorting (FACS) analysis with fluorescent-labeled antibodies against mouse CD3, mouse CD19, human CD124, and mouse CD124. (See, e.g., Blaeser et al. (2003) Targeted inactivation of the IL-4 receptor a chain I4R motif promotes allergic airway inflammation, J Exp Med 198(8):1189-1200).

To demonstrate the ligand specificities and receptor functionalities, primary cells derived from humanized IL-4Rα mice were used. Bone marrow-derived macrophages were cultured using femoral bone marrow cells from wild-type and humanized IL-4Rα mice in DMEM containing 10% fetal bovine serum plus 20% L-cell conditioned medium for 7 days.

Cells were then treated individually with 20 ng/ml of mouse IL-4, mouse IL-13, human IL-4, human IL-13, or vehicle diluted in culture medium for 20 hours. Quadruplicate samples from each condition were harvested for gene expression analysis.

Total RNA from these samples was extracted and amplified into cRNA by incorporating Cy3-CTP. Cy3 labeled cRNA from each sample was then hybridized to a custom Agilent array comprising of 43,538 60-mer oligos covering mouse transcriptomes. Data were extracted from scanned array images using Agilent Feature Extraction Software 9.5.

Differentially expressed genes between experimental groups were identified using Student's t-test (p<0.05, fold change ≥1.5). An expression cluster of these genes was generated using the Pearson correlation clustering algorithm from GeneSpring GX7.3.

The neutralizing effect of dupilumab against IL-4 was evaluated using an in vitro IgE class-switching assay with primary B cells isolated from humanized IL-4Rα (Il4ra$^{hu/hu}$) mice.

Wild-type (WT) and humanized IL-4Rα (Il4ra$^{hu/hu}$) mice received a high volume (hydrodynamic) driven gene delivery of naked plasmid DNA solution for the expression of mouse IL-25 in vivo. (See, e.g., Liu et al. (1999) Hydrodynamics-based transfection in animals by systemic administration of plasmid DNA, Gene Therapy 6:1258-1266.) Peripheral blood was collected 8 days later to measure serum murine IgE (mIgE) levels using a commercial ELISA kit (R & D systems, MN).

Purified primary B cells from humanized mouse splenocytes were activated with bacterial LPS and mixed with increasing amounts of recombinant human IL-4 in a 7 day culture to induce immunoglobulin class switching. For the antibody blockade experiment, purified B cells were incubated with increasing doses of dupilumab for 30 minutes before adding 0.167 nM recombinant human IL-4 and cultured for 7 days. IgE production in the absence of IL-4 or with isotype control mAb is shown in (◇) and (Δ), respectively. The murine IgE levels in the culture supernatants were measured using a commercial ELISA kit. (See, e.g., Moon et al. (1989) Regulation of IgG1 and IgE synthesis by interleukin 4 in mouse B cells, Scand I Immunol 30:355-361.)

Interleukin-25 (IL-25) is a cytokine produced by Th2 cells whose main activities are mediated through the production of IL-4 and IL-13 to induce tissue specific pathologies, such as increased pulmonary mucus production and goblet cell hyperplasia. (See Fort et al. (2001) IL-25 induces IL-4, IL-5, and IL-13 and Th2-associated pathologies in vivo, Immunity 15(6):985-995.)

Lack of IL-13 protects animals from IL-25 induced pathologies in target organ. Therefore, an IL-25 driven pulmonary inflammation model was used to assess the pharmacodynamic (PD) properties of dupilumab in vivo in mice comprising humanized IL-4 and/or IL-4Rα genes.

The PD responses of dupilumab on type II receptors were characterized using an IL-25-induced inflammation method by measuring pulmonary mucus accumulation in the humanized IL-4Rα (Il4ra$^{hu/hu}$) mice.

On Day 0, WT and humanized IL-4Rα (Il4ra$^{hu/hu}$) mice received the hydrodynamic delivery of mouse IL-25 expression vector and followed by an injection of dupilumab or isotype control mAb at the indicated doses. Additional doses of antibodies were administered every other day for a total of 4 doses. On day 8, lung tissues were collected from euthanized mice and processed lung sections were stained by periodic acid-Schiff before blinded scoring for pathological changes.

Results

The humanized IL-4Rα mice were characterized to show: (a) expression of human IL-4Rα on primary cells from doubly humanized IL-4/IL-4Rα (Il4$^{hu/hu}$/Il4ra$^{hu/hu}$) mice (see FIG. 3); (b) the change of IL-4 ligand specificities in humanized IL-4Rα (Il4ra$^{hu/hu}$) mice (see FIG. 4); and (c) the functionality of the IL-13 pathway in the humanized IL-4Rα (Il4ra$^{hu/hu}$) mice (see FIG. 4).

Figure 3:
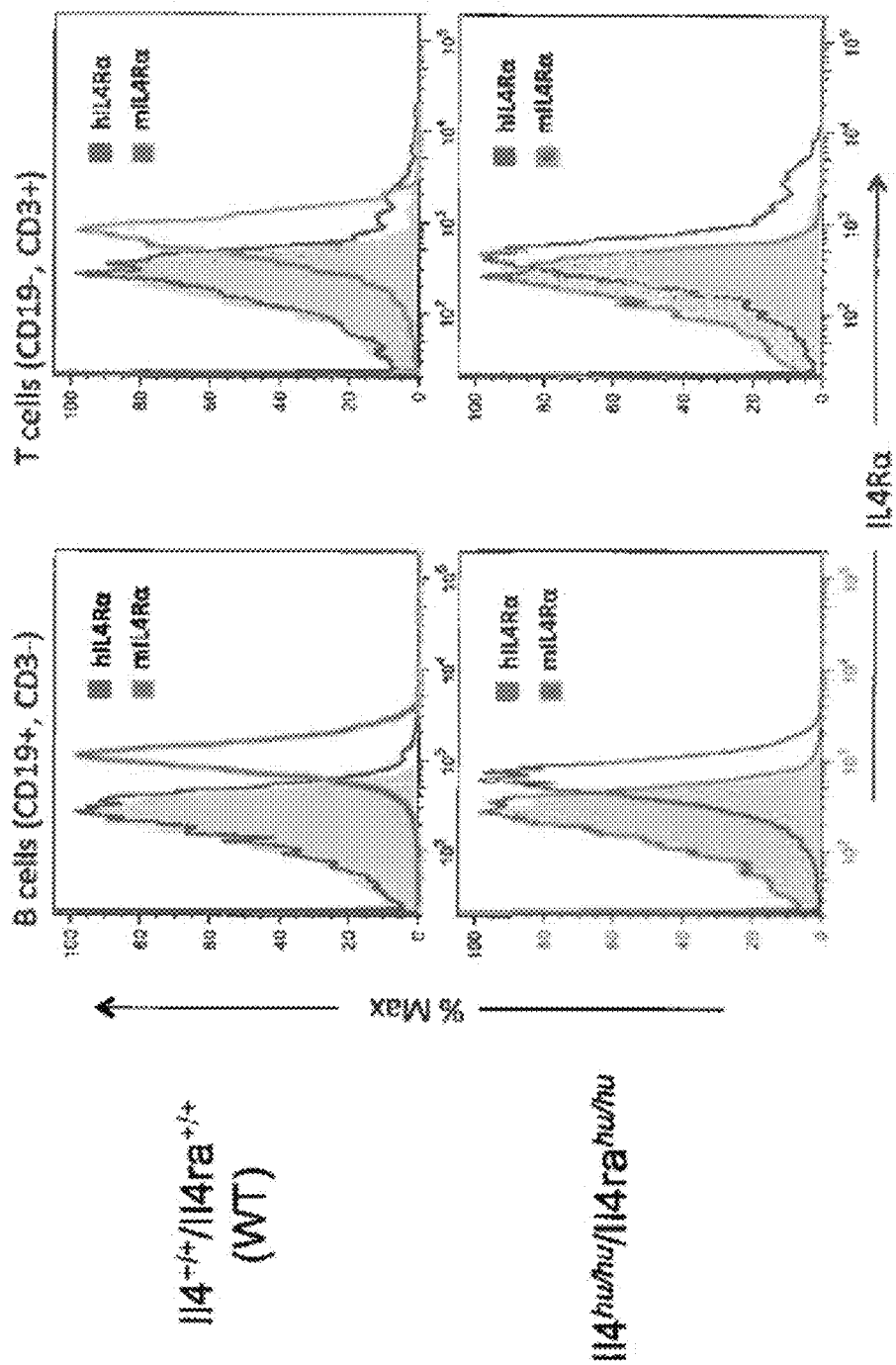
FIG. 3 shows the expression of humanized IL-4Rα protein on B and T cells from doubly humanized IL-4/IL-4Rα (Il4$^{hu/hu}$/Il4ra$^{hu/hu}$) mice.

As shown in FIG. 3, in which labeled profiles of IL-4Rα (CD124) on gated B and T cell populations are shown and the distribution of corresponding unstained cell population is shown in the shaded area, wild-type and humanized IL-4Rα (Il4ra$^{hu/hu}$) mice express similar amounts of IL-4Rα protein on the surface of B (CD19$^+$, CD3$^-$) and T (CD19$^-$, CD3$^+$) cells.

Figure 4:
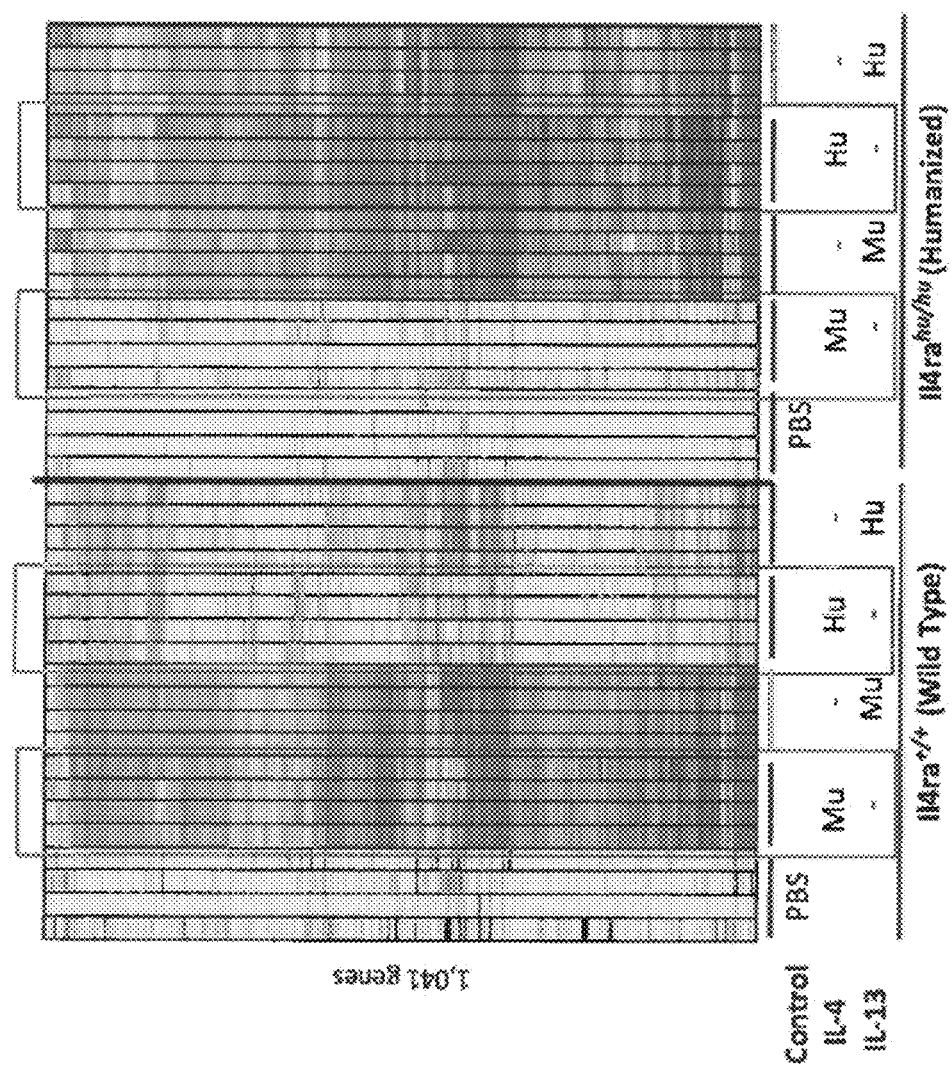
FIG. 4 shows the IL-4 and IL-13 ligand specificities and receptor functionalities using primary cells derived from humanized IL4Rα (Il4ra$^{hu/hu}$) mice.

As shown in FIG. 4 (left side), wild-type (Il4ra$^{+/+}$) mice respond to mouse, but not human, IL-4, and respond to both mouse and human IL-13. As shown in FIG. 4 (right side), humanized IL-4Rα (Il4ra$^{hu/hu}$) mice respond to human, but not mouse, IL-4, and respond to both mouse and human IL-13.

This data shows that IL-4, but not IL-13, displays species-specificity in wild-type and humanized IL-4Rα (Il4ra$^{hu/hu}$) mice.

Figure 5:
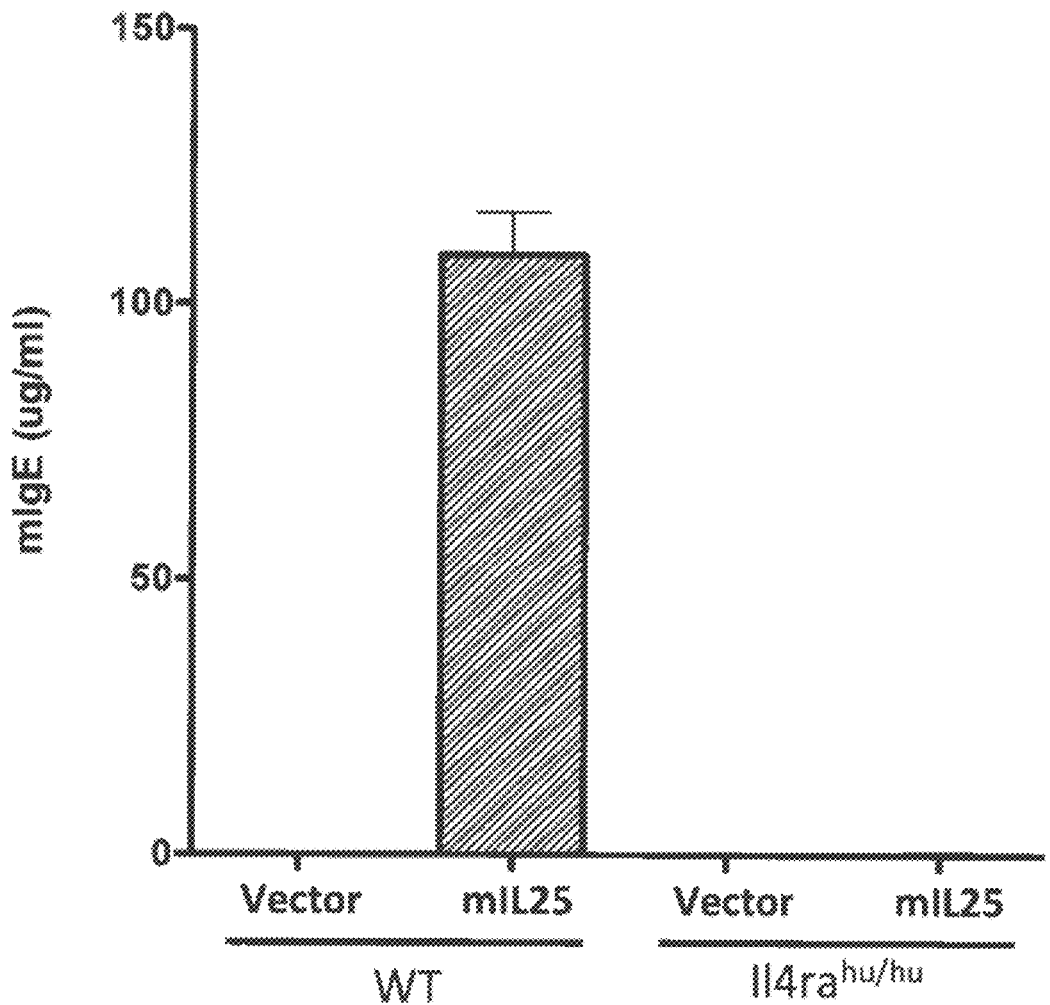
FIG. 5 shows IL-4 dependent IgE production in vivo in wild-type, but not humanized IL4Rα (Il4ra$^{hu/hu}$) mice.

As shown in FIG. 5, the role of IL-4 as the major factor mediating IgE class switching was supported by the lack of elevated levels of circulating IgE after mouse IL-25 gene delivery in humanized IL-4Rα (Il4ra$^{hu/hu}$) mice.

The dupilumab monoclonal antibody was investigated in vitro and in vivo.

Figure 6:
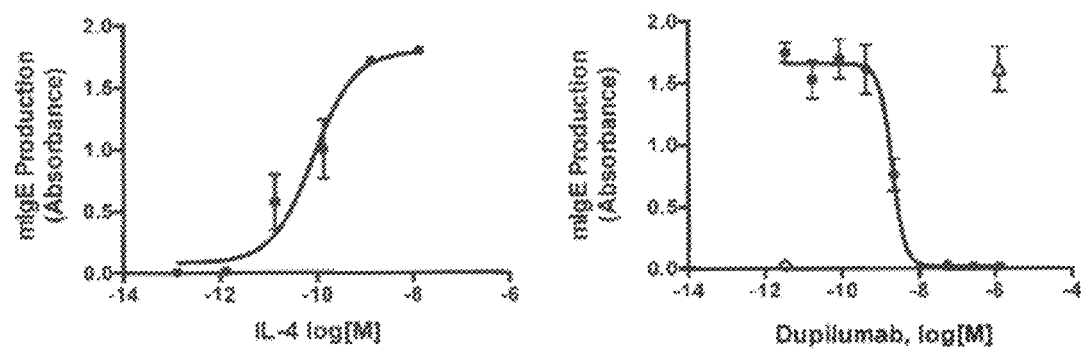
FIG. 6 shows that dose-dependent IL-4 induction of mIgE production ex vivo in mouse B cells (left panel) is blocked by dupilumab, in a dose-dependent manner (right panel).

As shown in FIG. 6, dupilumab prevents human IL-4 induced IgE production in humanized IL-4Rα (Il4ra$^{hu/hu}$) mice-derived primary B cell cultures.

Figure 7:
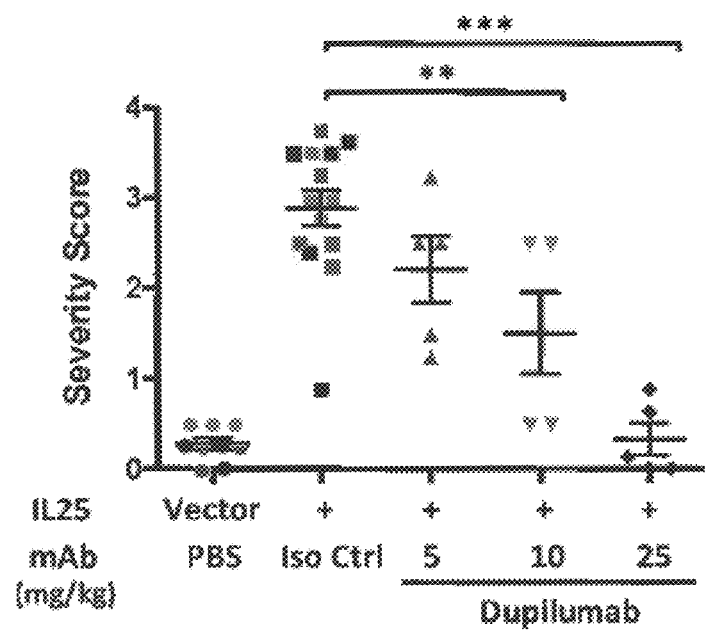
FIG. 7 shows that dupilumab, in a dose-dependent manner, prevents IL-25 induced lung pathologies in vivo in humanized IL4Rα (Il4ra$^{hu/hu}$) mice.

As shown in FIG. 7, dupilumab dose dependently reduced IL-25 induced pulmonary pathologies at 10 mg/kg and above (25 mg/kg reduced mucus pathology Conclusions The results demonstrate the pharmacological activity of dupilumab, a fully human anti-human IL-4Rα monoclonal antibody, in a genetically modified mouse model with cytokine-induced inflammation.

Generation of genetically modified mice with human IL-4 and/or IL-4Rα gene replacements provides a powerful tool to evaluate function of gene orthologs and in vivo efficacy of antibody candidates with limited cross-species reactivity.

Example 5

House Dust Mite Extract (HDM) Induced Pulmonary Inflammation Model

Figure 8:
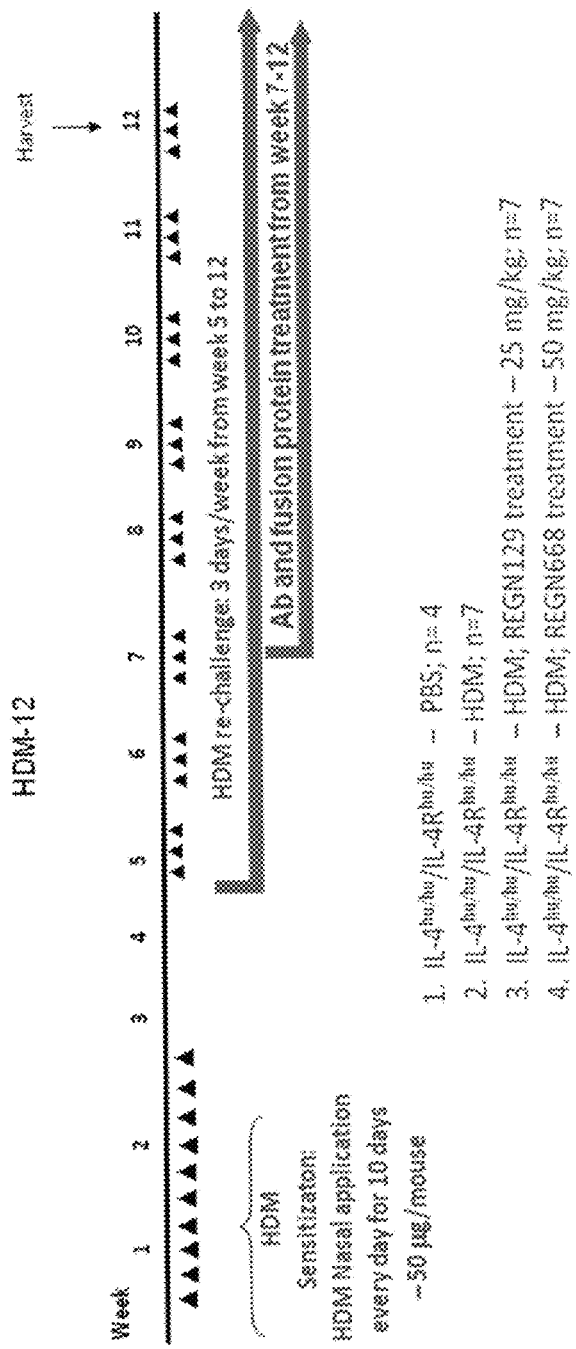
FIG. 8 shows the experimental design for assessing the therapeutic efficacy of dupilumab in a house dust mite extract (HDM) induced pulmonary inflammation model using doubly humanized IL-4 and IL-4Rα (IL-4$^{hu/hu}$/IL-4R$^{hu/hu}$) mice. "REGN668" refers to a human monoclonal antibody directed to human IL-4Rα, also known as dupilumab. "REGN129" refers to a mouse sol IL-13Rα2-Fc, which is a fusion protein between the ectodomain of mouse IL-13R2α and Fc.

Chronic airway inflammation in doubly humanized IL-4 and IL-R4α mice is induced by intranasal challenge of house dust mite (HDM) extract (Greer laboratories). In brief, mice were first sensitized by intranasal instillation of HDM suspension (20 µl at the concentration of 2.5 µg/ml) for 10 days. After a two-week interval of resolution, mice were re-challenged with intranasal HDM application 3 times per week between week 5 and 12. The treatment of dupilumab (anti-IL4Rα antibody) was started from the 7th week at the frequency of twice weekly by subcutaneous injections until the end of experiment at week 12. Tissue samples were collected for further analyses. The experimental design is depicted in FIG. 8.

Demonstrating the Therapeutic Efficacy of Dupilumab in the HDM Induced Airway Inflammation Model Using Doubly Humanized IL-4 and IL-4Rα Mice Airway disease was induced in doubly humanized IL-4 and IL-4Rα (IL-4ra$^{hu/hu}$/Il4ra$^{hu/hu}$) mice using the protocol described above. The histological analysis of lung tissue showed that intranasal HDM instillation caused increased production of mucus in the airway. Treatment of dupilumab reduced the mucus accumulation in the HDM challenged mice. Analysis of the infiltrating cells in bronchoalveolar lavage fluid (BALF) indicates that the eosinophil counts were increased by the HDM instillation and were reduced by the treatment of dupilumab. The total circulating IgE was elevated by the treatment of HDM in the humanized mice, suggesting a competent IL-4 signaling pathway. Use of dupilumab was capable of reducing the level of IgE. In contrast, a comparator molecule, IL13R2α-Fc, which antagonizes IL-13 only without interfering the IL-4 signal transduction, had comparable activities in reducing mucus accumulation and preventing eosinophil infiltration. Nonetheless, a differential effect was detected in the circulating IgE level between dupilumab and the IL-13 antagonist, IL13R2α-Fc. Blockade of IL-13 pathway alone was insufficient to reduce the HDM induced IgE level; whereas dupilumab reduced the production of IgE, a main pathogenic mediator of allergy, by blocking both the IL-4 and IL-13 pathways.

Figure 9:
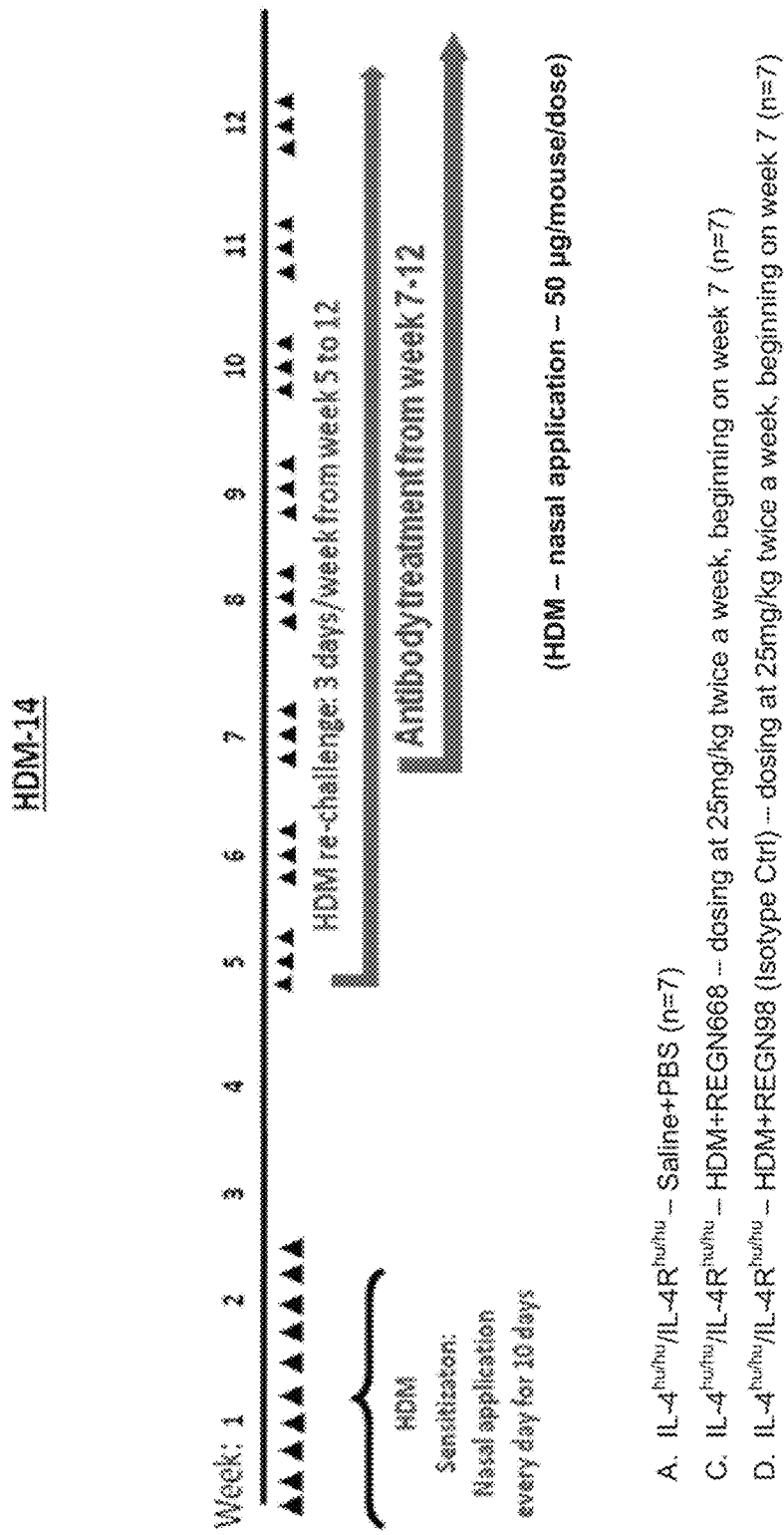
FIG. 9 shows the experimental design for assessing the therapeutic efficacy of dupilumab in an HDM induced pulmonary inflammation model using doubly humanized IL-4 and IL-4Rα (Il-4$^{hu/hu}$/Il-4R$^{hu/hu}$) mice and an isotype control antibody.

In a separate set of experiments, airway disease was induced in doubly humanized IL-4 and IL-4Rα (IL-4$^{hu/hu}$/IL-4R$^{hu/hu}$) mice using the same protocol described above, except that a different control was used. An isotype control antibody of the same IgG isotype as dupilumab was used in these experiments. The experimental design is depicted in FIG. 9. mRNA was purified from total RNA using Dynabeads mRNA kit (Life Tech) and strand specific RNA-Seq library was prepared from mRNA using Scriptseq RNA Library Prep kit (Illumina). The library was sequenced using HiSeq 2000 (Illumina) at read length of 33 bp and gene expression levels were extracted from the raw reads using Clcbio (Qiagen) RNA-Seq workflow. Differentially expressed genes between experimental groups were identified using Student's t-test (p<0.05, fold change ≥1.5). An expression cluster of these genes was generated using the Pearson correlation clustering algorithm from GeneSpring GX7.3. HDM was found to induce alteration of pulmonary gene expression in the doubly humanized IL-4 and IL-4Rα mice and such alteration was blocked by dupilumab. Serum samples were collected from euthanized mice at the end of the treatment period. The serum murine IgE levels were measured using a commercial ELISA kit (R & D systems). Statistical analysis was performed using ordinary one-way ANOVA method.

Example 6

Antigen Induced Cutaneous Inflammation Model

Chronic skin inflammation in doubly humanized Il-4 and Il-4Rα mice can be induced by the following procedure. The back hair of humanized mice is shaved with electric clipper and then stripped with adhesive tape to create minor injuries and break skin barrier. A gauze patch soaked with a solution of allergen (such as ovalbumin plus bacterial toxin or house dust mite extract) is attached to the skin for one week followed by two weeks of resolution period. The procedure is repeated three times for a total of 7 weeks to induce atopic dermatitis like skin lesions. The treated mice will have increased IgE levels, pruritis, thickening of the epidermis, typical symptoms of atopic dermatitis.

Example 7

Characterizing PK Profiles of Anti-Human IL-4Rα Antibodies in Mice Expressing Humanized IL-4Rα

This Example describes experiments conducted to evaluate the PK profiles of REGN 668 (human monoclonal antibody directed to human IL-4Rα, also known as "dupilumab") and control antibody REGN646 (monkey surrogate, anti-mfIL-4R non-binding control antibody).

The mice used in these experiments were MAID 1444 (homozygous for humanized IL-4Rα, or "IL-4Rα HumIn", in which the IL-4Rα ectodomain is human and the transmembrane and cytoplasmic regions are mouse) and strain-matched (75% C57BL/6/25%129Sv) wild-type ("WT") mice of 20-23 weeks. The study group included a total of 40 mice, male and female, with a cohort size per drug/per dose of 5 homozygous and 5 strain-matched WT. The antibodies (in PBS buffer) were given to mice via subcutaneous injection at 10 mg/kg. Blood samples were taken for analysis on the day of the injection (time point "0" or day 0), at 6 hr post injection, and on day 1, day 3, day 7, day 10, day 14, day 21, and day 30, respectively.

The circulating drug (i.e., REGN668 or REGN646) levels were determined by total human antibody analysis using an ELISA immunoassay. Briefly, a goat anti-human IgG polyclonal antibody (Jackson ImmunoResearch, #109-005-098) was coated onto 96-well plates to capture the tested human antibodies in the sera, and then plate-bound antibodies were detected using a goat anti-human IgG polyclonal antibody conjugated with horseradish peroxidase (Jackson ImmunoResearch, #109-035-098) and TMB substrate (BD Pharmingen). The serum samples were in six-dose serial dilutions per sample ranging from 1:100-1:243,000 and reference standards of the respective antibodies were in 12-dose serial dilutions. Drug antibody concentrations in the sera were calculated based on the reference standard curve generated using Graphpad Prism software.

The half-life of REGN 668 was found to be shortened in IL-4Rα HumIn mice as compared to wild-type mice with only mouse IL-4Rα protein. This difference in PK profiles could be explained by the target mediated interaction and clearance between monoclonal antibodies and human IL-4α receptor. Therefore, mice expressing human or humanized IL-4Rα provide suitable simulation to characterize the PK properties of anti-human IL-4Rα antibodies (e.g., dupilumab) in a preclinical mouse model.

Uses for Humanized IL-4 and/or IL-4Rα Mice

Humanized IL-4 and/or IL-4Rα are useful to evaluate the pharmacodynamics (PD) of human-specific IL-4 and/or IL-4Rα antagonists, e.g., neutralizing anti-IL-4 and/or anti-IL-4Rα antibodies, e.g., dupilumab.

Pharmacokinetics (PK) and PD assays in humanized IL-4 and/or IL-4Rα mice are performed according to standard procedures known in the art.

Humanized IL-4 and/or IL-4Rα mice are useful to test the in vivo therapeutic efficacy of human-specific IL-4 and/or IL-4Rα antagonists, e.g., neutralizing anti-IL-4 and/or IL-4Rα antibodies, e.g., dupilumab, in a variety of disease models known in the art, e.g., as shown hereinabove.

Example 8

Replacement of the Endogenous Mouse IL-33 Gene with a Human IL-33 Gene

The mouse IL-33 gene (NCBI Gene ID: 77125, Primary source: MGI:1924375; RefSeq transcript: NM_001164724.1; UniProt ID: Q8BVZ5; Genomic assembly: NCBI37/mm9; Location: chr19:29,999,604-30,035, 205+ strand) has 8 exons and encodes a protein of 266 amino acids (GenBank Accession No. NP_001158196.1).

The human IL-33 gene (NCBI Gene ID: 90865, Primary source: HGNC:16028; RefSeq transcript: NM_033439.3; UniProt ID: O95760; Genomic assembly: GRCh37/hg19; Location: chr9:6,215,149-6,257,983+ strand) also has 8 exons and encodes a protein of 270 amino acids (GenBank Accession No. NP_254274.1).

Figure 10A:
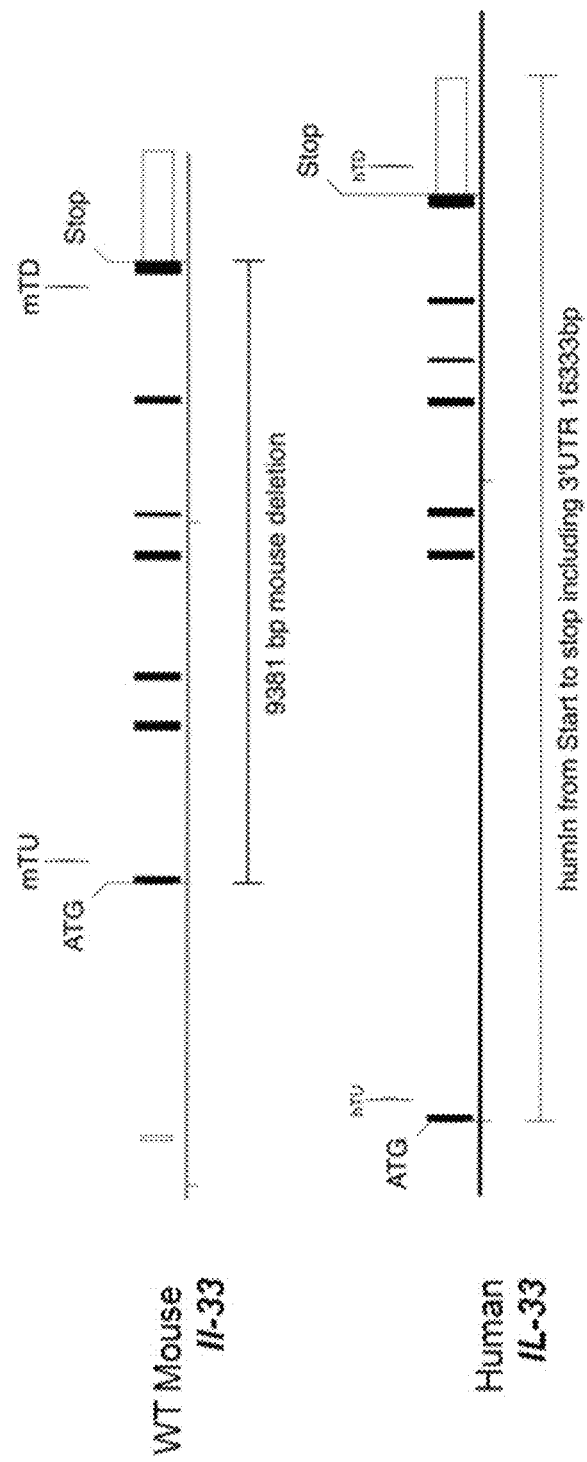
FIGS. 10A-10C illustrate the strategies for humanization of the mouse IL-33 locus.

A 16333 bp human genomic segment containing exon 2 starting from the ATG initiation codon through exon 8 (including the 3' untranslated region) of the human IL-33 gene replaced 9381 bp of the mouse IL-33 gene locus spanning exon 2 starting from the ATG initiation codon through the coding portion of exon 8 including the stop codon. See FIG. 10A.

Figure 10B:
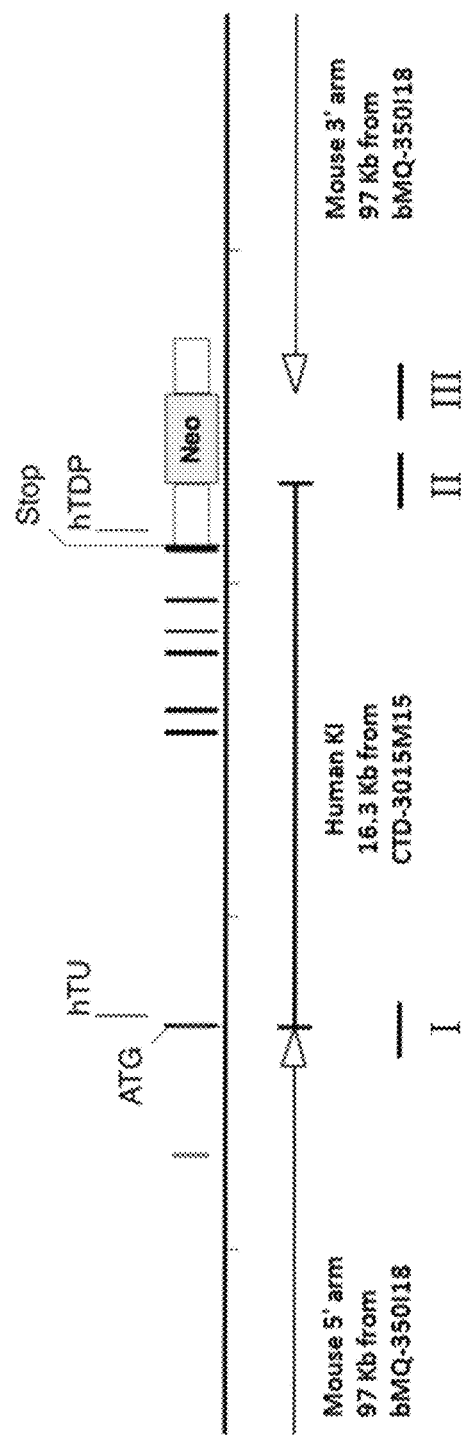

A targeting construct for replacing the mouse IL-33 gene with a human IL-33 genomic segment in a single targeting step was constructed using VelociGene® genetic engineering technology (see Valenzuela et al. (2003) High-throughput engineering of the mouse genome coupled with high-resolution expression analysis, Nature Biotech, 21(6):652-659), similar to the procedure described in Example 1 above for replacing the mouse IL-4 gene with a human IL-4 genomic segment, except that mouse and human IL-33 DNA were obtained from bacterial artificial chromosome (BAC) clones bMQ-350I18 and CTD-3015M15, respectively, and that the targeting vector contained a loxP neomycin selection cassette (FIG. 10B).

Correctly targeted ES cell clones (MAID 7060) were identified by a loss-of-native-allele (LONA) assay (Valenzuela et al. 2003) in which the number of copies of the native, unmodified IL-33 gene were determined by two TaqMan™ quantitative polymerase chain reactions (qPCRs) specific for sequences in the mouse IL-33 gene that were targeted for deletion. The qPCR assays comprised the following primer-probe sets (written 5' to 3'):

```
upstream ("mTU"):
                                      (SEQ ID NO: 31)
forward primer, TTGGACTAGTAACAAGAAGGGTAGCA;

(SEQ ID NO: 32)
reverse primer, CCTTTCCCATCACCCTCTAACTT;

(SEQ ID NO: 33)
probe (MGB), AGCTCTGGTGGACAGA;

downstream ("mTD"):
                                      (SEQ ID NO: 34)
forward primer, TCTCTGCCAAGCTGCTTATCC;

(SEQ ID NO: 35)
reverse primer, GGCTGCATGGAAGAGGTGAA;

(SEQ ID NO: 36)
probe (MGB), CTCTCCACAAATCG.
```

Confirmation that the human IL-33 gene sequence replaced the mouse IL-33 gene sequence in the humanized allele was confirmed by a TaqMan™ qPCR assay that comprises the following primer-probe sets (written 5' to 3'):

```
upstream ("hTU")
                                      (SEQ ID NO: 37)
forward primer, CAGGCAGGAATAGCTGAGATAATCT;

(SEQ ID NO: 38)
reverse primer, TGTGGAGCAAAAAGTGGTTGAT;

(SEQ ID NO: 39)
probe (MGB), CCTGTGAATAGTGATAAAC;

downstream ("hTD"):
                                      (SEQ ID NO: 40)
forward primer, CAGTTCCAAACGATAGGCTCAA;

(SEQ ID NO: 41)
reverse primer, ATAATTCTGTGAAGCATCTGGTCTTC;

(SEQ ID NO: 42)
probe (MGB), CTAGAGCTGCTAGTAAAA.
```

The upstream junction of the murine IL-33 locus and the sequence containing the human IL-33 gene (shown as "I" in FIG. 10B) is designed to be within 5'-ATAGCCAAGG TTGCTTCTGA TGACTTCAGG TCCATATAGT TGGAT-TAATG TTATATTTCA ATCCCACAGA AACCTGAAAA *ATG* AAGCCTA AAATGAAGTA TTCAACCAAC AAAATTTCCA CAGCAAAGTG GAAGAACACA GCAAGCAAAG CCTTGTGTTT-3' (SEQ ID NO: 43), wherein the human IL-33 sequence is italicized and the human start codon ATG is underlined. The downstream junction of the sequence containing the human IL-33 genomic sequence and the loxP neomycin selection cassette (shown as "II" in FIG. 10B) is designed to be within

```
                                      (SEQ ID NO: 44)
5'-TTTATATTAT TGAATAAAGT ATATTTTCCA AATGTATGTG

AGACTATAAT GATTTTATCA TATGATGACT CAATATTCTG/

CTCGAGATAA CTTCGTATAA TGTATGCTAT ACGAAGTTAT

Figure 10C:
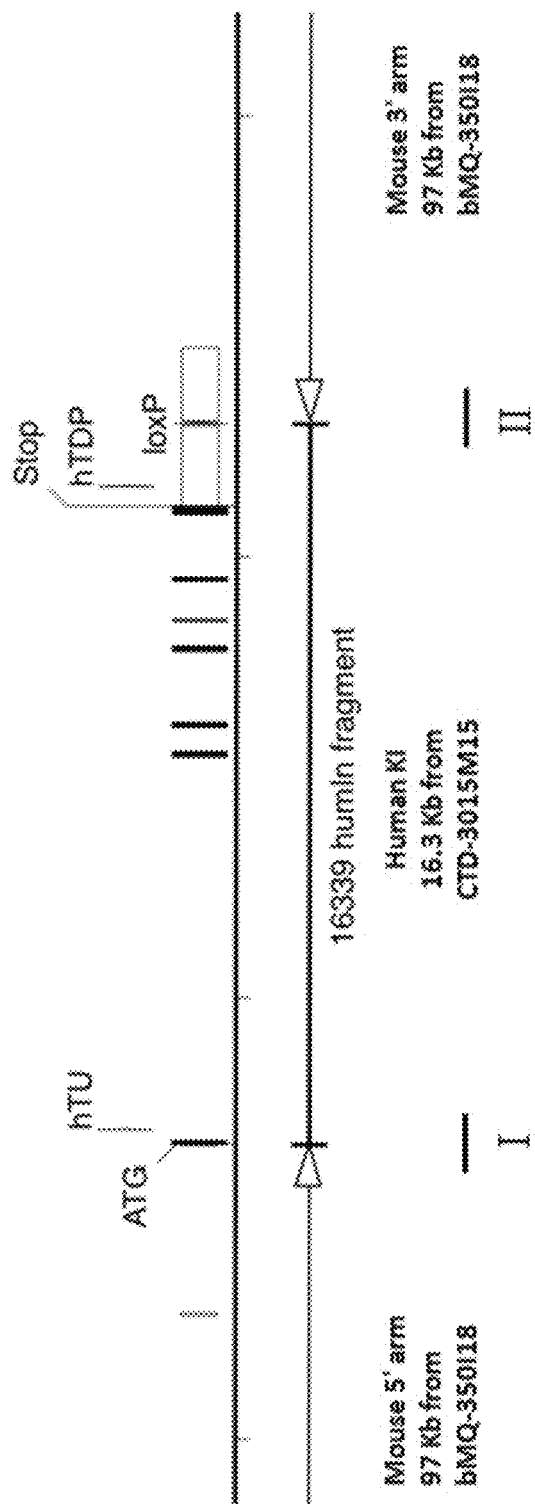

ATGCATGGCC TCCGCGCCGG GTTTTGGCGC CTCCCGCGGG-3',
``` wherein the human IL-33 sequence is italicized and the junction is indicated by the "/" symbol, and the lox P site is underlined. The downstream junction of the sequence of the loxP neo selection cassette and the murine IL-33 locus (shown as "III" in FIG. 10C) is designed to be within

```
                                      (SEQ ID NO: 45)
5'-AGCCCCTAGA TAACTTCGTA TAATGTATGC TATACGAAGT

TATGCTAGTA ACTATAACGG TCCTAAGGTA GCGAGCTAGC/

CGCCTGTGCG TTCTGGGTTG AATGACTTAA TGCTTCCAAC

TGAAGAAAGG GTAACAGAGA GAAAGAAAGC CATTCTTGGC-3',
``` wherein the junction is shown by the "/" symbol, and the loxP site is underlined.

Correctly targeted ES cells (MAID 7060) were further electroporated with a transient Cre-expressing vector to remove the drug selection cassette and obtain ES cell clones without drug cassette (MAID 7061). The upstream junction in these MAID 7061 ES cells (shown as "I" in FIG. 18C) is the same as in MAID 7060 ES cells. The downstream junction (shown as "II" in FIG. 18C) is designed to be within wherein the 3' human IL-33 sequence is italicized before the first "/" symbol, and the mouse IL-33 3' sequence is italicized after the second "/" symbol, and the loxP site is underlined.

(SEQ ID NO: 46),

```
5'-TTTATATTAT TGAATAAAGT ATATTTTCCA AATGTATGTG

AGACTATAAT GATTTTATCA TATGATGACT CAATATTCTG/

CTCGAGATAA CTTCGTATAA TGTATGCTAT ACGAAGTTAT

GCTAGTAACT ATAACGGTCC TAAGGTAGCG AGCTAGC/

CGCCTGTGCG TTCTGGGTTG AATGACTTAA TGCTTCCAAC

TGAAGAAAGG GTAACAGAGA GAAAGAAAGC CATTCTTGGC-3'
```

Correctly targeted ES cells (MAID 7060 or MAID 7061) were introduced into an 8-cell stage SW mouse embryo by the VelociMouse® method (see, U.S. Pat. Nos. 7,294,754, 7,576,259, 7,659,442, and Poueymirou et al. (2007) F0 generation mice that are essentially fully derived from the donor gene-targeted ES cells allowing immediate phenotypic analyses, Nature Biotech. 25(1):91-99). VelociMice® (F0 mice fully derived from the donor ES cell) bearing the humanized IL-33 gene were identified by genotyping for loss of mouse allele and gain of human allele using a modification of allele assay (see, Valenzuela et al. (2003)). The same LONA assay was used to assay DNA purified from tail biopsies for mice derived from the targeted ES cells to determine their IL-33 genotypes and confirm that the humanized IL-33 allele had transmitted through the germline. Two pups heterozygous for the replacement were bred to generate a mouse that is homozygous for the replacement of the endogenous mouse IL-33 gene by the human IL-33 gene.

What is claimed is:

1. A rodent, comprising a replacement of a genomic DNA of a rodent IL-4Rα gene at an endogenous rodent IL-4Rα locus with a human genomic DNA of a human IL-4Rα gene to form a humanized IL-4Rα gene, wherein the genomic DNA of the rodent IL-4Rα gene comprises the ATG initiation codon of exon 1 through exon 5 of the rodent IL-4Rα gene, and the human genomic DNA of the human IL-4Rα gene comprises the ATG initiation codon of exon 1 through exon 5 of the human IL-4Rα gene; wherein the humanized IL-4Rα gene comprises the ATG initiation codon of exon 1 through exon 5 of the human IL-4Rα gene and exons 6-9 of the rodent IL-4Rα gene, and the human genomic DNA present in the humanized IL-4Rα gene begins with the ATG initiation codon in exon 1 of the human IL-4Rα gene; and wherein expression of the humanized IL-4Rα gene is under control of the rodent IL-4Rα promoter at the endogenous rodent IL-4Rα locus, wherein the rodent is a mouse or a rat.

2. The rodent of claim 1, wherein the rodent is a mouse that is incapable of expressing a mouse IL-4Rα protein.

3. The rodent of claim 1, wherein the rodent expresses a human or humanized IL-4 protein.

4. The rodent of claim 3, wherein the rodent comprises a replacement of a genomic DNA of a rodent IL-4 gene at an endogenous rodent IL-4 locus with a genomic DNA of a human IL-4 gene to form a humanized IL-4 gene, wherein the genomic DNA of the rodent IL-4 gene comprises the ATG initiation codon of exon 1 through exon 4 of the rodent IL-4 gene, and the genomic DNA of the human IL-4 gene comprises the ATG initiation codon of exon 1 through exon 4 of the human IL-4 gene, and wherein expression of the humanized IL-4 gene is under control of the rodent IL-4 promoter at the endogenous rodent IL-4 locus.

5. The rodent of claim 1, wherein the rodent is a mouse.

6. A method for making a humanized rodent, comprising replacing a genomic DNA of a rodent IL-4Rα gene at an endogenous rodent IL-4Rα locus with a human genomic DNA of a human IL-4Rα gene to form a humanized IL-4Rα gene, wherein the genomic DNA of the rodent IL-4Rα gene comprises the ATG initiation codon of exon 1 through exon 5 of the rodent IL-4Rα gene, and the human genomic DNA of the human IL-4Rα gene comprises the ATG initiation codon of exon 1 through exon 5 of the human IL-4Rα gene; wherein the humanized IL-4Rα gene comprises the ATG initiation codon of exon 1 through exon 5 of the human IL-4Rα gene followed by exons 6-9 of the rodent IL-4Rα gene, and the human genomic DNA present in the humanized IL-4Rα gene begins with the ATG initiation codon of exon 1 of the human IL-4Rα gene; and wherein the humanized IL-4Rα gene is operably linked to the rodent IL-4Rα promoter at the endogenous rodent IL-4Rα locus, wherein the rodent is a mouse or a rat.

7. The method of claim 6, wherein the rodent is a mouse.

8. The rodent of claim 3, wherein the rodent is a mouse that does not express a mouse IL-4 protein.

* * * * *

SEQUENCE LISTING

```
<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
catgcacgga gatggatgtg                                                    20

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
gacccctcag gtccacttac c                                                  21

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
<220> FEATURE:
<221> NAME/KEY: misc_feature
<222> LOCATION: (19)..(19)
<223> OTHER INFORMATION: Labled with BHQ: fluorescence quencher of the
      black hole quencher type

<400> SEQUENCE: 3
aacgtcctca cagcaacga                                                     19

<210> SEQ ID NO 4
<211> LENGTH: 19
```

```
<212> TYPE: DNA
<213> ORGANISM: Artificial Sequence
<220> FEATURE:
<223> OTHER INFORMATION: Synthetic Oligonucleotide

<400> SEQUENCE: 4
gtgcccaggt gtgctcatg                                              19

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 5
cgcctgcctc ctcactttat c                                           21

<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
<220> FEATURE:
<221> NAME/KEY: misc_feature
<222> LOCATION: (19)..(19)
<223> OTHER INFORMATION: Labled with BHQ: fluorescence quencher of the
      black hole quencher type

<400> SEQUENCE: 6
atctgcttca ccatccact                                              19

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 7
gcctggacca agactctgt                                              19

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
accgtgggac ggcttcttac                                             20

<210> SEQ ID NO 9
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
```

```
<220> FEATURE:
<221> NAME/KEY: misc_feature
<222> LOCATION: (19)..(19)
<223> OTHER INFORMATION: Labled with BHQ: fluorescence quencher of the
      black hole quencher type

<400> SEQUENCE: 9
caccgagttg accgtaacag acatc                                          25

<210> SEQ ID NO 10
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 10
tgcggccgat cttagcc                                                   17

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
ttgaccgatt ccttgcgg                                                  18

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
<220> FEATURE:
<221> NAME/KEY: misc_feature
<222> LOCATION: (21)..(21)
<223> OTHER INFORMATION: Labled with BHQ: fluorescence quencher of the
      black hole quencher type

<400> SEQUENCE: 12
acgagcgggt tcggcccatt c                                              21

<210> SEQ ID NO 13
<211> LENGTH: 458
<212> TYPE: DNA
<213> ORGANISM: Artificial Sequence
<220> FEATURE:
<223> OTHER INFORMATION: Nucleic acid sequence containing the upstream
      junction of Murine IL4 Locus and Human IL4 sequence

<400> SEQUENCE: 13
tgctgattgg cccagaataa ctgacaatct ggtgtaataa aatttttccaa tgtaaactca    60 ttttcccttg gtttcagcaa ctttaactct atatatagag agacctctgc cagcattgca   120
ttgttagcat ctcttgataa acttaattgt ctctcgtcac tgacggcaca gagctattga   180
tgggtctcac ctcccaactg cttccccctc tgttcttcct gctagcatgt gccggcaact   240
ttgtccacgg acacaagtgc gatatcacct tacaggagat catcaaaact ttgaacagcc   300
tcacagagca gaaggtgagt acctatctgg caccatctct ccagatgttc tggtgatgct   360
```

```
ctcagtattt ctaggcatga aaacgttaac agctgctaga gaagttggaa ctggtggttg    420
gtggcagtcc agggcacaca gcgaggcttc tccctgc                             458
```

<210> SEQ ID NO 14
<211> LENGTH: 565
<212> TYPE: DNA
<213> ORGANISM: Artificial Sequence
<220> FEATURE:
<223> OTHER INFORMATION: Nucleic acid sequence containing the downstream
      junction of Human IL4 sequence and floxed hygo selection cassett

<400> SEQUENCE: 14

```
tgtttatttt gcagaattcc tgtcctgtga aggaagccaa ccagagtacg ttggaaaact    60
tcttggaaag gctaaagacg atcatgagag agaaatattc aaagtgttcg agctgaatat    120
tttaatttat gagtttttga tagctttatt ttttaagtat ttatatattt ataactcatc    180
ataaaataaa gtatatatag aatctaacag caatggcatt taatgtattg ctatgtttta    240
cttgacaaat gaaattatgg tttgcaactt ttagggaaat caatttagtt taccaagaga    300
ctataaatgc tatgggagca aaacaggaaa gaccacttcc ccctcgaggg gttccctctc    360
gagttaggga cataacacac aagataatta agaacacaa ggccatacaa gatgcggccg    420
caccggtata acttcgtata aggtatccta tacgaagtta tatgcatggc ctccgcgccg    480
ggttttggcg cctcccgcgg gcgccccct cctcacggcg agcgctgcca cgtcagacga    540
agggcgcagc gagcgtcctg atcct                                          565
```

<210> SEQ ID NO 15
<211> LENGTH: 438
<212> TYPE: DNA
<213> ORGANISM: Artificial Sequence
<220> FEATURE:
<223> OTHER INFORMATION: Nucleic acid sequence containing the downstream
      junction of floxed hygo selection cassett and Murine IL-4 locus

<400> SEQUENCE: 15

```
tgccaagttc taattccatc agacctcgac ctgcagccgg cgcgccataa cttcgtataa    60
ggtatcctat acgaagttat ctcgagagga gttcccaccc ttctcaagag cataatgcgc    120
agatcattaa gggacagatg caggctgggg agacggttca gcagttagga gtacctgttg    180
ctcttccaga ggacccaggt tcaattcccg cactcacat agcagcttaa acaataact    240 caagttctgg gggagctgat gctctcctct ggcctcctgt ggaggtacac agaccacatg    300
cctgtaggca agacacccac acacataaaa acaaaataaa ataaggatag aaaggccagg    360
gggatgaatc cagaggtaga agaaaactta ttccctggaa ttgtcctctg actccctcc    420 caaaacctct aacacgca                                                  438
```

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16

```
ccgctggcat gtgtattgtg                                                20
```

<210> SEQ ID NO 17
<211> LENGTH: 21
<212> TYPE: DNA
<213> ORGANISM: Artificial Sequence

```
<220> FEATURE:
<223> OTHER INFORMATION: Synthetic Oligonucleotide

<400> SEQUENCE: 17
tgagtgtggg accctcaaga g                                            21

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
<220> FEATURE:
<221> NAME/KEY: misc_feature
<222> LOCATION: (24)..(24)
<223> OTHER INFORMATION: Labled with BHQ: fluorescence quencher of the
      black hole quencher type

<400> SEQUENCE: 18
tgacccaagc cctacatggc cact                                         24

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
tgaggagagc tcacgggaat c                                            21

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
acccatctcc tgcgtttctg                                              20

<210> SEQ ID NO 21
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
<220> FEATURE:
<221> NAME/KEY: misc_feature
<222> LOCATION: (25)..(25)
<223> OTHER INFORMATION: Labled with BHQ: fluorescence quencher of the
      black hole quencher type

<400> SEQUENCE: 21
ttgacacgcc agctacactg ctcca                                        25

<210> SEQ ID NO 22
<211> LENGTH: 21
<212> TYPE: DNA
```

```
<213> ORGANISM: Artificial Sequence
<220> FEATURE:
<223> OTHER INFORMATION: Synthetic Oligonucleotide

<400> SEQUENCE: 22
acctgcgtct ccgactacat g                                        21

<210> SEQ ID NO 23
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 23
gagctcggtg ctgcaattg                                           19

<210> SEQ ID NO 24
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
<220> FEATURE:
<221> NAME/KEY: misc_feature
<222> LOCATION: (25)..(25)
<223> OTHER INFORMATION: Labled with BHQ: fluorescence quencher of the
      black hole quencher type

<400> SEQUENCE: 24
tgggaccatt catcttccac tcgca                                    25

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
ggtggagagg ctattcggc                                           19

<210> SEQ ID NO 26
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 26
gaacacggcg gcatcag                                             17

<210> SEQ ID NO 27
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Labled with FAM: 5-carboxyfluorescein
      fluorescent probe
<220> FEATURE:
```

```
<221> NAME/KEY: misc_feature
<222> LOCATION: (23)..(23)
<223> OTHER INFORMATION: Labled with BHQ: fluorescence quencher of the
      black hole quencher type

<400> SEQUENCE: 27
tgggcacaac agacaatcgg ctg                                             23

<210> SEQ ID NO 28
<211> LENGTH: 243
<212> TYPE: DNA
<213> ORGANISM: Artificial Sequence
<220> FEATURE:
<223> OTHER INFORMATION: Portion of Murine IL-4Ralpha locus and sequence
      containing IL-4Ralpha gene

<400> SEQUENCE: 28
tgggggaggg aggccatgac acaaatgaaa tggaccccgc tgacccagga tcagcatctg     60
cccactcttc tttctgcagg caccttttgt gtccccaatg gggtggcttt gctctgggct    120
cctgttccct gtgagctgcc tggtcctgct gcaggtggca agctctggta agtcaccact    180
tctcaatcat tcatttgttg gctattaatg gcgtgccagg tcctgcagt atgtcacctg     240 gcc                                                                  243

<210> SEQ ID NO 29
<211> LENGTH: 243
<212> TYPE: DNA
<213> ORGANISM: Artificial Sequence
<220> FEATURE:
<223> OTHER INFORMATION: Nucleic acid sequence containing the downstream
      junction of Human IL-4Ralpha sequence and floxed neo selection
      cassett

<400> SEQUENCE: 29
gtcagatcgt ggagggtctc ggacgagggt cctgaccctg gtctccagt cctgggaagt      60 ggagcccagg ctgtaccatg gctgacctca gctcatggct cccgggctcg ataactataa    120
cggtcctaag gtagcgactc gagataactt cgtataatgt atgctatacg aagttatatg    180
catggcctcc gcgccgggtt ttggcgcctc ccgcgggcgc cccctcctc acggcgagcg     240 ctg                                                                  243

<210> SEQ ID NO 30
<211> LENGTH: 390
<212> TYPE: DNA
<213> ORGANISM: Artificial Sequence
<220> FEATURE:
<223> OTHER INFORMATION: Portion of the sequence of the floxed neo
      selection cassett and the Murine IL-4Ralpha locus

<400> SEQUENCE: 30
tattgttttg ccaagttcta attccatcag acctcgacct gcagcccta gataacttcg     60 tataatgtat gctatacgaa gttatcctag gttgagctc tctgtagcca ggtaaccaag    120
ggtcccaggg gaaccccag tgtggacgcg gactgcacat gacacagggc ggcctcccca    180
ttcatgactg ttttttctcct tgcagacttc cagctgcccc tgatacagcg ccttccactg   240
ggggtcacca tctcctgcct ctgcatcccg ttgttttgcc tgttctgtta cttcagcatt    300
accaagtgag ttcctgcttt ggctggtgtc tctggctggc ccttcagcag tgctctcaga    360
ggtcacagtc attgtgctgg ctgagaaaag                                    390

<210> SEQ ID NO 31
```

```
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 31
ttggactagt aacaagaagg gtagca                                          26

<210> SEQ ID NO 32
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 32
cctttcccat caccctctaa ctt                                             23

<210> SEQ ID NO 33
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 33
agctctggtg gacaga                                                     16

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 34
tctctgccaa gctgcttatc c                                               21

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
ggctgcatgg aagaggtgaa                                                 20

<210> SEQ ID NO 36
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 36
ctctccacaa atcg                                                       14

<210> SEQ ID NO 37
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 37
```
caggcaggaa tagctgagat aatct                                              25

<210> SEQ ID NO 38
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 38
tgtggagcaa aaagtggttg at                                                 22

<210> SEQ ID NO 39
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 39
cctgtgaata gtgataaac                                                     19

<210> SEQ ID NO 40
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 40
cagttccaaa cgataggctc aa                                                 22

<210> SEQ ID NO 41
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 41
ataattctgt gaagcatctg gtcttc                                             26

<210> SEQ ID NO 42
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 42
ctagagctgc tagtaaaa                                                      18

<210> SEQ ID NO 43
<211> LENGTH: 160
<212> TYPE: DNA
<213> ORGANISM: Artificial Sequence
<220> FEATURE:
<223> OTHER INFORMATION: Synthetic Oligonucleotide

<400> SEQUENCE: 43
atagccaagg ttgcttctga tgacttcagg tccatatagt tggattaatg ttatatttca        60
atcccacaga aacctgaaaa atgaagccta aaatgaagta ttcaaccaac aaaatttcca       120
cagcaaagtg gaagaacaca gcaagcaaag ccttgtgttt                             160

```
<210> SEQ ID NO 44
<211> LENGTH: 160
<212> TYPE: DNA
<213> ORGANISM: Artificial Sequence
<220> FEATURE:
<223> OTHER INFORMATION: Synthetic Oligonucleotide

<400> SEQUENCE: 44
tttatattat tgaataaagt atattttcca aatgtatgtg agactataat gattttatca      60
tatgatgact caatattctg ctcgagataa cttcgtataa tgtatgctat acgaagttat     120
atgcatggcc tccgcgccgg gttttggcgc ctcccgcggg                           160

<210> SEQ ID NO 45
<211> LENGTH: 160
<212> TYPE: DNA
<213> ORGANISM: Artificial Sequence
<220> FEATURE:
<223> OTHER INFORMATION: Synthetic Oligonucleotide

<400> SEQUENCE: 45
agcccctaga taacttcgta taatgtatgc tatacgaagt tatgctagta actataacgg      60
tcctaaggta gcgagctagc cgcctgtgcg ttctggtttg aatgacttaa tgcttccaac     120
tgaagaaagg gtaacagaga gaaagaaagc cattcttggc                           160

<210> SEQ ID NO 46
<211> LENGTH: 237
<212> TYPE: DNA
<213> ORGANISM: Artificial Sequence
<220> FEATURE:
<223> OTHER INFORMATION: Synthetic Oligonucleotide

<400> SEQUENCE: 46
tttatattat tgaataaagt atattttcca aatgtatgtg agactataat gattttatca      60
tatgatgact caatattctg ctcgagataa cttcgtataa tgtatgctat acgaagttat     120
gctagtaact ataacggtcc taaggtagcg agctagccgc ctgtgcgttc tgggttgaat     180
gacttaatgc ttccaactga agaagggta acagagagaa agaaagccat tcttggc        237
```